US011786107B2

(12) United States Patent
Tani

(10) Patent No.: US 11,786,107 B2
(45) Date of Patent: Oct. 17, 2023

(54) ENDOSCOPE APPARATUS, COMPRESSION METHOD, AND NON-TRANSITORY COMPUTER-READABLE RECORDING MEDIUM

(71) Applicant: OLYMPUS CORPORATION, Tokyo (JP)

(72) Inventor: Shinsuke Tani, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 628 days.

(21) Appl. No.: 17/038,075

(22) Filed: Sep. 30, 2020

(65) Prior Publication Data

US 2021/0121047 A1 Apr. 29, 2021

Related U.S. Application Data

(63) Continuation of application No. PCT/JP2019/007103, filed on Feb. 25, 2019.

(30) Foreign Application Priority Data

Apr. 3, 2018 (JP) .................................. 2018-071699

(51) Int. Cl.
*H04N 19/423* (2014.01)
*A61B 1/00* (2006.01)

(52) U.S. Cl.
CPC ...... *A61B 1/00016* (2013.01); *A61B 1/00006* (2013.01); *A61B 1/00009* (2013.01); *A61B 1/00045* (2013.01); *H04N 19/423* (2014.11)

(58) Field of Classification Search
CPC ............ A61B 1/00016; A61B 1/00006; A61B 1/00009; A61B 1/00045; H04N 19/423
(Continued)

(56) References Cited

U.S. PATENT DOCUMENTS 6,553,143 B2 * 4/2003 Miyake ................ H04N 19/146
382/250
7,022,067 B2 * 4/2006 Glukhovsky .......... A61B 1/045
348/700
(Continued)

FOREIGN PATENT DOCUMENTS

EP 3 222 199 A1 9/2017
JP 6125122 B1 5/2017
(Continued)

OTHER PUBLICATIONS

International Search Report dated Apr. 9, 2019 received in PCT/JP2019/007103.

*Primary Examiner* — Trang U Tran
(74) *Attorney, Agent, or Firm* — Scully, Scott, Murphy & Presser, P.C.

(57) ABSTRACT

An image compression device of an endoscope apparatus includes a compression processing control unit, a storage unit, a first compression parameter generating unit, a second compression parameter generating unit and a compression parameter determining unit. The first compression parameter generating unit generates a first tentative compression parameter based on a transferable data amount. The second compression parameter generating unit generates a second tentative compression parameter based on a storage capacity of the storage unit. The compression parameter determining unit compares the first tentative compression parameter and the second tentative compression parameter to select a parameter with which a data amount after compression becomes smaller as a selected parameter. The compression processing control unit updates a compression parameter with the selected parameter and performs compression processing using the updated compression parameter.

18 Claims, 12 Drawing Sheets

(58) Field of Classification Search
USPC .......................................................... 348/65
See application file for complete search history.

(56) References Cited

U.S. PATENT DOCUMENTS

| | | | | |
|---|---|---|---|---|
| 7,106,909 | B2* | 9/2006 | Satoh | H04N 19/152 |
| | | | | 375/E7.176 |
| 7,227,998 | B2* | 6/2007 | Nakayama | H04N 1/41 |
| | | | | 375/E7.139 |
| 9,377,776 | B2* | 6/2016 | Nakamura | G05B 19/4103 |
| 10,945,592 | B2* | 3/2021 | Takenouchi | A61B 1/05 |
| 2010/0231736 | A1* | 9/2010 | Hosokawa | H04N 19/61 |
| | | | | 348/222.1 |
| 2017/0251904 | A1 | 9/2017 | Kasumi | |
| 2018/0220873 | A1 | 8/2018 | Tani | |
| 2018/0365836 | A1* | 12/2018 | Liao | G06V 10/235 |
| 2021/0105467 | A1* | 4/2021 | Tani | A61B 1/045 |

FOREIGN PATENT DOCUMENTS

| | | |
|---|---|---|
| JP | 6192882 B1 | 9/2017 |
| JP | 6253600 B2 | 12/2017 |
| WO | 2017/029839 A1 | 2/2017 |
| WO | 2017/061495 A1 | 4/2017 |

* cited by examiner

ENDOSCOPE APPARATUS, COMPRESSION METHOD, AND NON-TRANSITORY COMPUTER-READABLE RECORDING MEDIUM

CROSS REFERENCE TO RELATED APPLICATION

This application is a continuation application of PCT/JP2019/007103 filed on Feb. 25, 2019 and claims benefit of Japanese Application No. 2018-071699 filed in Japan on Apr. 3, 2018, the entire contents of which are incorporated herein by this reference.

BACKGROUND OF THE INVENTION

1. Field of the Invention

The present invention relates to an endoscope apparatus including an image compression device configured to compress image data, a compression method and a non-transitory computer-readable recording medium.

2. Description of the Related Art

In recent years, endoscope apparatuses have widely been used in the medical field and the industrial field. In particular, endoscopes used in the medical field have widely been used in, e.g., an observation of an organ inside a body cavity, a medical treatment using a treatment instrument or a surgical operation under an endoscopic observation.

Moreover, in recent years, battery-driven endoscopes with a rechargeable battery mounted are beginning to be put into practical use by advancement in semiconductor technology and power consumption reduction by use of an LED as a light source for illumination. Each battery-driven endoscope incorporates a wireless communication unit configured to perform wireless communication with a processor, and is configured to wirelessly transmit image data of an image picked up by an image pickup device.

An amount of data that is transferable via a wireless communication (hereinafter also referred to as "transferable data amount") is defined under the specifications of the wireless communication. In an endoscope apparatus including a battery-driven endoscope, in order to make a data amount of image data transmitted wirelessly be equal to or smaller than the transferable data amount, the image data is transmitted after compression of the image data.

When a compression rate of the image data is increased to reduce a data amount of the image data, the image data can stably be transmitted wirelessly and power consumed by the endoscope can be reduced. However, an increase in compression rate of the image data causes deterioration in image quality of the image data. Therefore, if high-quality image data is required, it is desirable to control the compression rate, such as decreasing the compression rate, as necessary.

Japanese Patent No. 6192882 describes an endoscope system in which a compression rate of image data is controlled based on a scene in which a surgeon is going to perform an endoscopic procedure. Japanese Patent No. 6253600 describes an endoscope system in which a compression rate of image data is controlled based on pixel value distribution characteristics determined by image pickup characteristics of an image pickup device and spectral characteristics of an object.

SUMMARY OF THE INVENTION

An endoscope apparatus according to an aspect of the present invention includes: an image pickup device configured to pick up an image of an object and generate an image data item; and an image compression device configured to compress the image data item, and the image compression device including a storage element having a storage capacity of a predetermined size, and the image compression device is configured to perform compression processing for each of a plurality of unit areas of the image data item using a compression parameter to generate a plurality of compressed data items from the image data item that is one image data item, store each of the plurality of compressed data items in the storage element, generate a first compression parameter for performing compression processing in such a manner that a calculated data amount calculated by performing an arithmetic operation including calculation of a total sum of respective data amounts of the plurality of compressed data items becomes equal to or smaller than a first target data amount defined based on a transferable data amount that is an amount of data transferable in a transmission path for the image data item, generate a second compression parameter for performing compression processing in such a manner that a maximum value of the respective data amounts of the plurality of compressed data items becomes equal to or smaller than a second target data amount defined based on the storage capacity, compare the first compression parameter and the second compression parameter to select a parameter with which a data amount after compression is smaller as a selected parameter, and update the compression parameter with the selected parameter.

A compression method according to an aspect of the present invention is a compression method for compressing an image data item generated by an image pickup device of an endoscope, the compression method including: performing compression processing for each of a plurality of unit areas of the image data item using a compression parameter to generate a plurality of compressed data items from the image data item that is one image data item, and storing each of the plurality of compressed data items in a storage element having a storage capacity of a predetermined size; generating a first compression parameter for performing compression processing in such a manner that a calculated data amount calculated by performing an arithmetic operation including calculation of a total sum of respective data amounts of the plurality of compressed data items stored becomes equal to or smaller than a first target data amount defined based on a transferable data amount that is an amount of data transferable in a transmission path for the image data item; generating a second compression parameter for performing compression processing in such a manner that a maximum value of the respective data amounts of the plurality of compressed data items becomes equal to or smaller than a second target data amount defined based on the storage capacity; comparing the first compression parameter and the second compression parameter to select a parameter with which a data amount after compression is smaller as a selected parameter; and compressing a newly acquired image data item using the compression parameter.

A non-transitory computer-readable recording medium according to an aspect of the present invention is a non-transitory computer-readable recording medium recording a program for a computer to execute, the program being provided to compress an image data item generated by an image pickup device of the endoscope, the program causing the computer to: perform compression processing for each of a plurality of unit areas of the image data item using a compression parameter to generate a plurality of compressed data items from the image data item that is one image data item, and store each of the plurality of compressed data items in a storage element having a storage capacity of a predetermined size; generate a first compression parameter for performing compression processing in such a manner that a calculated data amount calculated by performing an arithmetic operation including calculation of a total sum of respective data amounts of the plurality of compressed data items stored becomes equal to or smaller than a first target data amount defined based on a transferable data amount that is an amount of data transferable in a transmission path for the image data item; generate a second compression parameter for performing compression processing in such a manner that a maximum value of the respective data amounts of the plurality of compressed data items becomes equal to or smaller than a second target data amount defined based on the storage capacity; compare the first compression parameter and the second compression parameter to select a parameter with which a data amount after compression is smaller as a selected parameter; and compress a newly acquired image data item using the compression parameter.

DETAILED DESCRIPTION OF THE PREFERRED EMBODIMENTS

Embodiments of the present invention will be described below with reference to the drawings.

First Embodiment (Configuration of Endoscope Apparatus)

Figure 1:
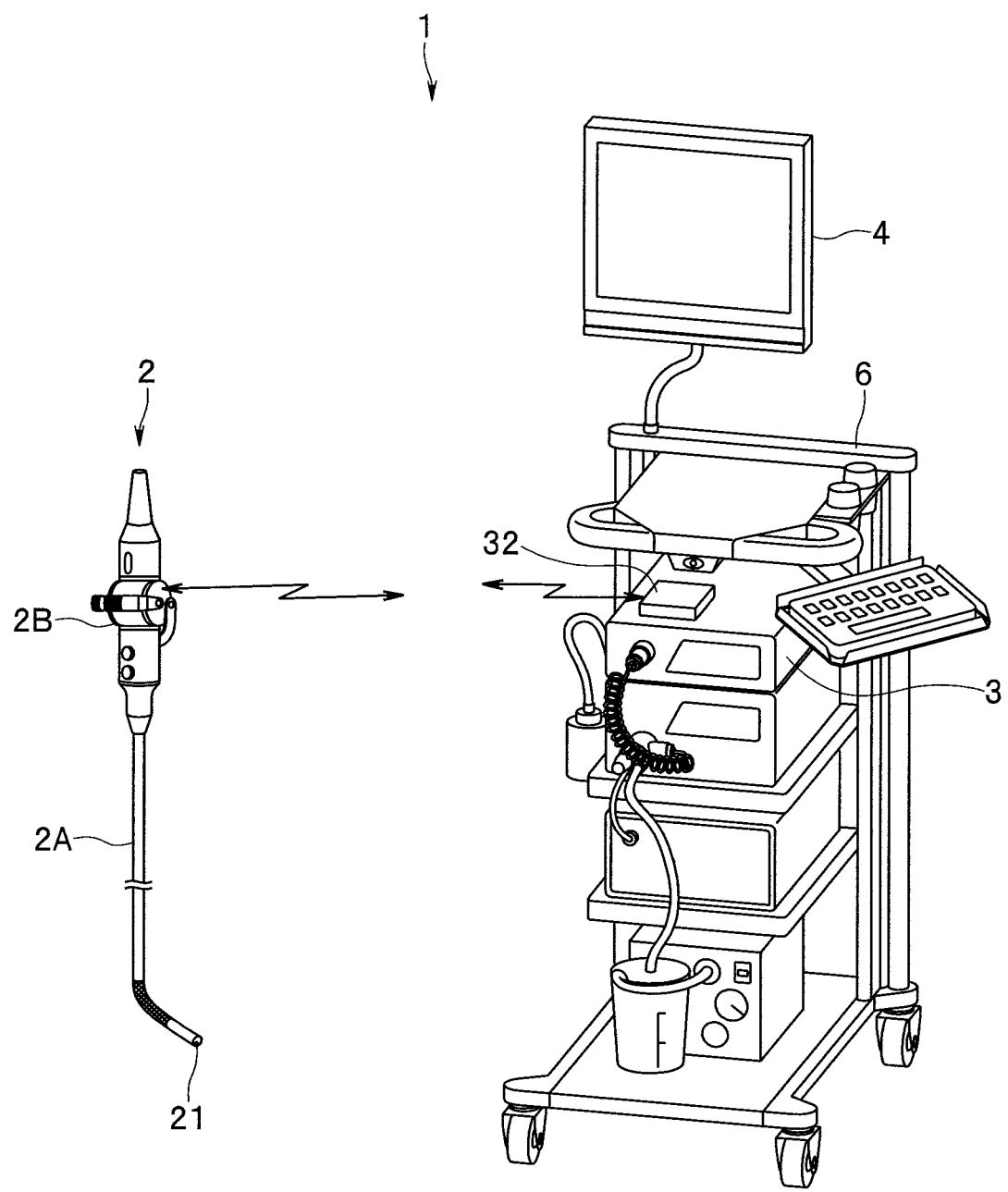
FIG. 1 is an explanatory diagram illustrating an overall configuration of an endoscope apparatus according to a first embodiment of the present invention.

First, a schematic configuration of an endoscope apparatus according to a first embodiment of the present invention will be described. FIG. 1 is an explanatory diagram illustrating an overall configuration of an endoscope apparatus 1 according to the present embodiment. The endoscope apparatus 1 according to the present embodiment is a wireless endoscope apparatus including a wireless endoscope 2, which is a battery-driven portable endoscope. Hereinafter, the wireless endoscope 2 is simply referred to as "endoscope 2".

The endoscope apparatus 1 further includes a processor 3, which is a video processor physically separated from the endoscope 2, and a monitor 4, which is a display unit connected to the processor 3. The processor 3 is wirelessly connected to the endoscope 2 and performs predetermined image processing to be described later. The monitor 4 displays, e.g., a result of the image processing, more specifically, an image picked up by the endoscope 2.

Note that as illustrated in FIG. 1, in a surgery room, the processor 3, the monitor 4 and various medical devices are placed on a cart 6. Examples of the medical devices placed on the cart 6 include, e.g., devices such as an electrical scalpel device, an insufflation device and a video recorder and a carbon dioxide-filled gas cylinder.

The endoscope 2 includes an elongated insertion portion 2A to be inserted into a body cavity, an operation portion 2B provided at a proximal end portion of the insertion portion 2A, and an image pickup unit 21 configured to pick up an image of an object and generate an image data item. The image pickup unit 21 includes a non-illustrated image pickup device, such as a CCD or CMOS image sensor, provided in a distal end portion of the insertion portion 2A.

Figure 2:
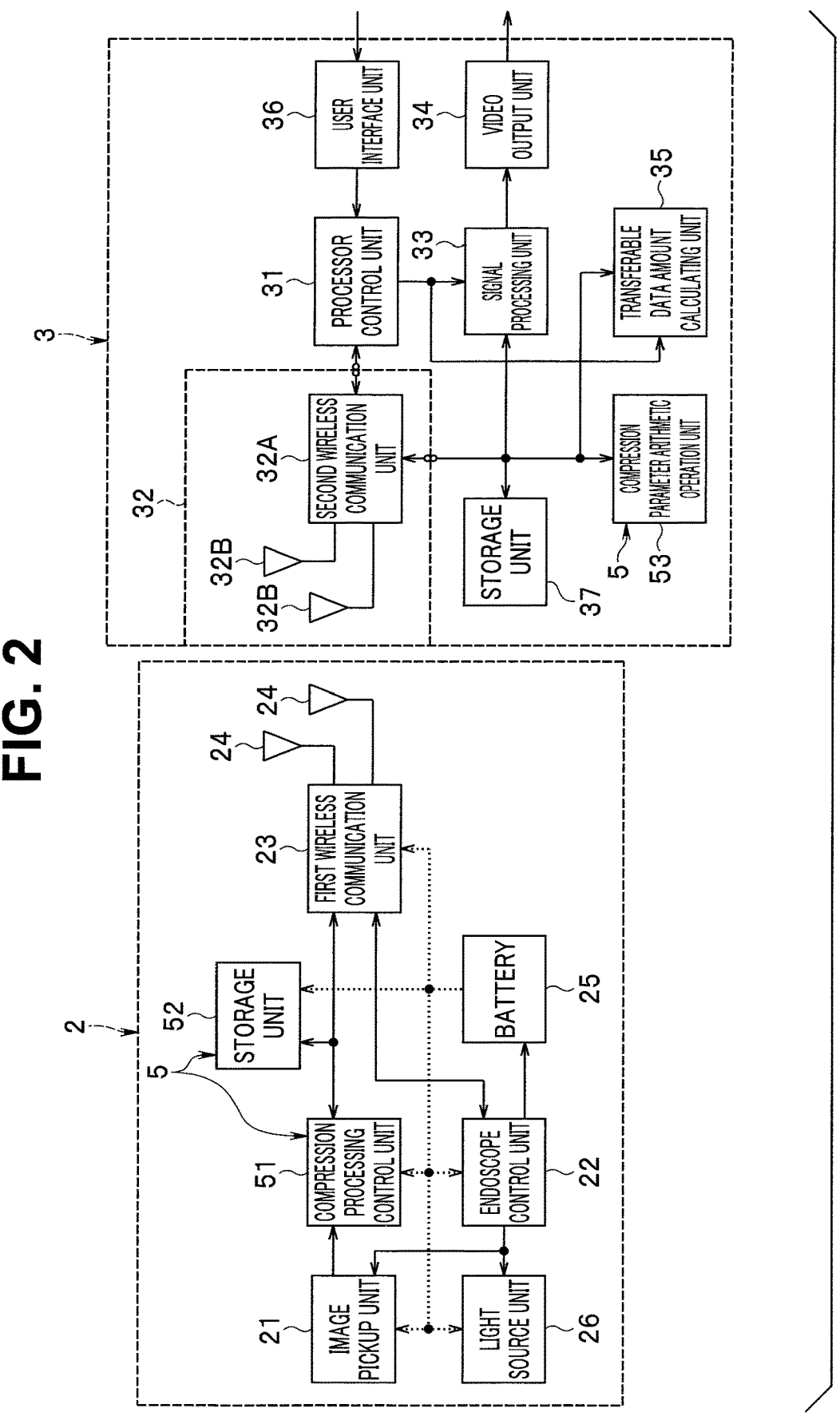
FIG. 2 is a functional block diagram illustrating configurations of an endoscope, a processor and an image compression device in the endoscope apparatus according to the first embodiment of the present invention.

The endoscope apparatus 1 further includes an image compression device 5 configured to compress the image data item generated by the image pickup unit 21. Note that the image compression device 5 is illustrated in FIG. 2 mentioned later. In the present embodiment, a transmission path through which the image data item is transmitted includes a wireless transmission path.

(Configurations of Endoscope, Processor and Image Compression Device)

Next, configurations of the endoscope 2, the processor 3 and the image compression device 5 will be described in detail with reference to FIG. 2. FIG. 2 is a functional block diagram illustrating the configurations of the endoscope 2, the processor 3 and the image compression device 5. In the present embodiment, a part of the image compression device 5 is provided in the endoscope 2, and another part of the image compression device 5 is provided in the processor 3. As illustrated in FIG. 2, the image compression device 5 includes a compression processing control unit 51 and a storage unit 52 provided in the endoscope 2, and a compression parameter arithmetic operation unit 53 provided in the processor 3.

The configuration of the endoscope 2, and the compression processing control unit 51 and the storage unit 52 will be described below. As illustrated in FIG. 2, the endoscope 2 includes the image pickup unit 21, an endoscope control unit 22, a first wireless communication unit 23, antennae 24, a battery 25 and a light source unit 26. Note that since the endoscope 2 is a part of the endoscope apparatus 1, the endoscope apparatus 1 can be regarded as including the first wireless communication unit 23 and the first wireless communication unit 23 can be regarded as being provided in the endoscope 2.

The battery 25 is configured to be capable of being loaded in the operation portion 2B (see FIG. 1). Moreover, the battery 25 is configured to be capable of, after being loaded in the operation portion 2B, supplying power to the image pickup unit 21, the endoscope control unit 22, the first wireless communication unit 23, the light source unit 26, the compression processing control unit 51 and the storage unit 52 as a power supply unit.

The endoscope control unit 22 controls respective circuit units inside the endoscope 2 and controls the battery 25 to supply power to the respective units inside the endoscope 2. The endoscope control unit 22 is configured by, for example, a central processing unit (hereinafter referred to as "CPU") or a digital signal processor (hereinafter referred to as "DSP").

The light source unit 26 is configured by a non-illustrated light-emitting element, such as a light-emitting diode, provided in the operation portion 2B (see FIG. 1), and generates illuminating light for illuminating the inside of a body cavity. The illuminating light is guided to a distal end of the insertion portion 2A (see FIG. 1) by a non-illustrated light guide and is applied to an object via a non-illustrated lens provided in the distal end of the insertion portion 2A. The object is, for example, a region, such as a diseased part, inside a subject.

Return light of the illuminating light from the object forms an image on an image pickup surface of the image pickup device of the image pickup unit 21. The image pickup unit 21 generates an image data item based on the optical image of the object, by means of photoelectric conversion and outputs the image data item to the compression processing control unit 51.

The compression processing control unit 51 performs predetermined compression processing for the image data item generated by the image pickup unit 21 to generate a plurality of compressed data items. The storage unit 52 has a storage capacity for storing compressed data items, the storage capacity having a predetermined size, and sequentially stores each of the plurality of compressed data items. In the present embodiment, the storage capacity is constant. Moreover, the storage unit 52 is further configured to be capable of storing a selected parameter to be described later. The compression processing control unit 51 is configured by, for example, a CPU or a DSP. The storage unit 52 is configured by at least a part of a rewritable storage element, such as a RAM, provided in the endoscope 2. The content of the compression processing will be described later.

The first wireless communication unit 23 includes a non-illustrated wireless transmission circuit configured to generate a signal to be transmitted wirelessly and a non-illustrated wireless reception circuit configured to demodulate a signal received wirelessly, and wirelessly transmits/receives predetermined signals to/from the processor 3 via the antennae 24. The predetermined signals include the plurality of compressed data items stored in the storage unit 52 and a selected parameter to be described later. Note that the first wireless communication unit 23 may be configured to be capable of performing wireless communication using a plurality of frequency bands, for example, a 60-GHz band and a 5-GHz band. The 60-GHz band is used for, for example, transmitting/receiving compressed data items. The 5-GHz band is used for, for example, transmitting/receiving information including a selected parameter.

Next, the configuration of the processor 3, and the compression parameter arithmetic operation unit 53 will be described. As illustrated in FIG. 2, the processor 3 includes a processor control unit 31, a wireless receiver 32, a signal processing unit 33, a video output unit 34, a transferable data amount calculating unit 35, a user interface unit (hereinafter referred to as "user IF unit") 36 and a storage unit 37. Note that since the processor 3 is a part of the endoscope apparatus 1, the endoscope apparatus 1 can be regarded as including the signal processing unit 33 and the transferable data amount calculating unit 35.

The wireless receiver 32 may be incorporated in the processor 3 or may be configured separately from a body of the processor 3. In the latter case, the wireless receiver 32 is configured to be connected to the body of the processor 3 by a non-illustrated connector. FIG. 1 illustrates an example in which the wireless receiver 32 is configured separately from the body of the processor 3.

The wireless receiver 32 includes a second wireless communication unit 32A and antennae 32B. Note that since the wireless receiver 32 is a part of the processor 3 and the processor 3 is a part of the endoscope apparatus 1, the endoscope apparatus 1 can be regarded as including the second wireless communication unit 32A and the second wireless communication unit 32A can be regarded as being provided in the processor 3.

The second wireless communication unit 32A includes a non-illustrated wireless transmission circuit configured to generate a signal to be transmitted wirelessly, and a non-illustrated wireless reception circuit configured to demodulate a signal received wirelessly, and transmits/receives predetermined signals to/from the endoscope 2 via the antennae 32B. The predetermined signals include the plurality of compressed data items transmitted by the first wireless communication unit 23 and the selected parameter to be described later. Note that as with the first wireless communication unit 23, the second wireless communication unit 32A may be configured to be capable of performing wireless communication using a plurality of frequency bands, for example, a 60-GHz band and a 5-GHz band.

The storage unit 37 has a storage capacity of a predetermined size and sequentially stores each of the plurality of compressed data items received by the second wireless communication unit 32A. Moreover, the storage unit 37 is further configured to be capable of storing the selected parameter to be described later. The storage unit 37 is configured by at least a part of a rewritable storage element, such as a RAM, provided in the processor 3.

The signal processing unit 33 reads each of the plurality of compressed data items from the storage unit 37 and performs predetermined image processing for the plurality of compressed data items. More specifically, the signal processing unit 33 performs decompression processing for each of the plurality of compressed data items and combine the decompressed data items to generate a non-compressed image data item. Hereinafter, the non-compressed image data item generated by the signal processing unit 33 is referred to as "decompressed image data item". The decompressed image data item is outputted to the video output unit 34.

The video output unit 34 converts the decompressed image data item into a format in which the image data item can be displayed on the monitor 4, and outputs the converted image data item to the monitor 4 (see FIG. 1). The monitor 4 displays the decompressed image data item as a result of the image processing in the signal processing unit 33.

The transferable data amount calculating unit 35 successively calculates a transferable data amount that is an amount of data transferrable via a transmission path through which an image data item is transmitted. The transferable data amount is defined, for example, as an amount of data transferable during a period of time necessary for transmission of an image data item for one frame. In the present embodiment, the transmission path includes a wireless transmission path formed between an antenna 24 and an antenna 32B.

A transferable data amount in a wireless communication is defined by specifications of the wireless communication, and varies depending on an environment of the wireless communication. In the present embodiment, the transferable data amount calculating unit 35 calculates a transferable data amount based on an environment of a wireless communication. More specifically, for example, it is possible to make the endoscope 2 and the processor 3 transmit/receive data for calculation while changing an amount of the data and calculate a transferable data amount based on the data amount of the data for calculation, the data being successfully transmitted/received. Note that the data for calculation may be the image data item generated by the image pickup unit 21. In this case, the signal processing unit 33 and the transferable data amount calculating unit 35 are configured in such a manner that a data amount of the image data item resulting from the decompression by the signal processing unit 33 is outputted to the transferable data amount calculating unit 35.

The compression parameter arithmetic operation unit 53 generates a selected parameter by performing an arithmetic operation sequence relating to a compression parameter used in the compression processing control unit 51, based on the plurality of compressed data items stored in the storage unit 37. A configuration of the compression parameter arithmetic operation unit 53 and the arithmetic operation sequence relating to the compression parameter will be described later.

The user IF unit 36 is an interface configured to receive a user operation. More specifically, the user IF unit 36 is configured by, for example, a front panel and various buttons for a control system, and outputs an operation signal based on a user operation to the processor control unit 31. Examples of the user operation include designation of an observation mode of the endoscope 2, settings relating to image display and setting of an initial value of the compression parameter to be described later. Note that a user IF unit may be provided in the endoscope 2 so that the observation mode of the endoscope 2 can be designated via at least one of the user IF unit 36 of the processor 3 and the user IF unit of the endoscope 2.

The processor control unit 31 controls the respective circuit units inside the processor 3 and controls a non-illustrated power supply unit to supply power to the respective units inside the processor 3. Moreover, based on an operation signal input from the user IF unit 36, the processor control unit 31 can provide various instructions to the endoscope control unit 22 provided in the endoscope 2, via wireless communication between the endoscope 2 and the processor 3. Each of the processor control unit 31, the signal processing unit 33, the transferable data amount calculating unit 35 and the compression parameter arithmetic operation unit 53 is configured by, for example, a processor including hardware, such as a CPU or a DSP.

(Configuration of Compression Parameter Arithmetic Operation Unit)

Figure 3:
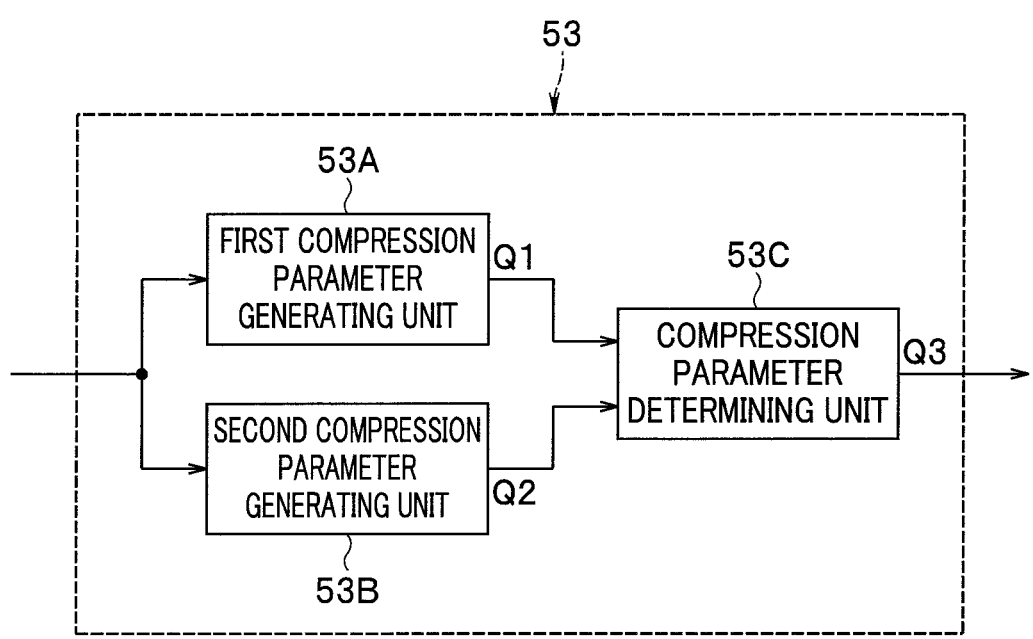
FIG. 3 is a functional block diagram illustrating a configuration of a compression parameter arithmetic operation unit in the first embodiment of the present invention.

Next, a configuration of the compression parameter arithmetic operation unit 53 will be described with reference to FIG. 3. FIG. 3 is a functional block diagram illustrating a configuration of the compression parameter arithmetic operation unit 53. The compression parameter arithmetic operation unit 53 includes a first compression parameter generating unit 53A, a second compression parameter generating unit 53B and a compression parameter determining unit 53C. Note that since the compression parameter arithmetic operation unit 53 is a part of the image compression device 5, the image compression device 5 can be regarded as including a first compression parameter generating unit 53A, a second compression parameter generating unit 53B and a compression parameter determining unit 53C. Moreover, since the compression parameter arithmetic operation unit 53 is provided in the processor 3, the first compression parameter generating unit 53A, the second compression parameter generating unit 53B and the compression parameter determining unit 53C can be regarded as being provided in the processor 3.

The first compression parameter generating unit 53A is configured to be capable of acquiring respective data amounts of the plurality of compressed data items stored in the storage unit 37 (see FIG. 2). As a part of the arithmetic operation sequence relating to the compression parameter, the first compression parameter generating unit 53A generates a first tentative compression parameter Q1 based on the respective data amounts of the plurality of compressed data items generated from the image data item that is one image data item. The first tentative compression parameter Q1 is outputted to the compression parameter determining unit 53C.

The second compression parameter generating unit 53B is configured to be capable of acquiring a maximum value of each of the respective data amounts of the plurality of compressed data items stored in the storage unit 37. As a part of the arithmetic operation sequence relating to the compression parameter, the second compression parameter generating unit 53B generates a second tentative compression parameter Q2 based on the maximum values of the respective data amounts of the plurality of compressed data items generated from the image data item that is one image data item. The second tentative compression parameter Q2 is outputted to the compression parameter determining unit 53C.

As a part of the arithmetic operation sequence relating to the compression parameter, the compression parameter determining unit 53C compares the first tentative compression parameter Q1 and the second tentative compression parameter Q2 and selects either one of these tentative compression parameters as a selected parameter Q3. In the present embodiment, the selected parameter Q3 is outputted to the storage unit 37 and the storage unit 52 provided in the endoscope 2.

Operation of the compression parameter arithmetic operation unit 53, that is, the arithmetic operation sequence relating to the compression parameter will be described later.

(Image Data Processing in Endoscope)

Figure 4:
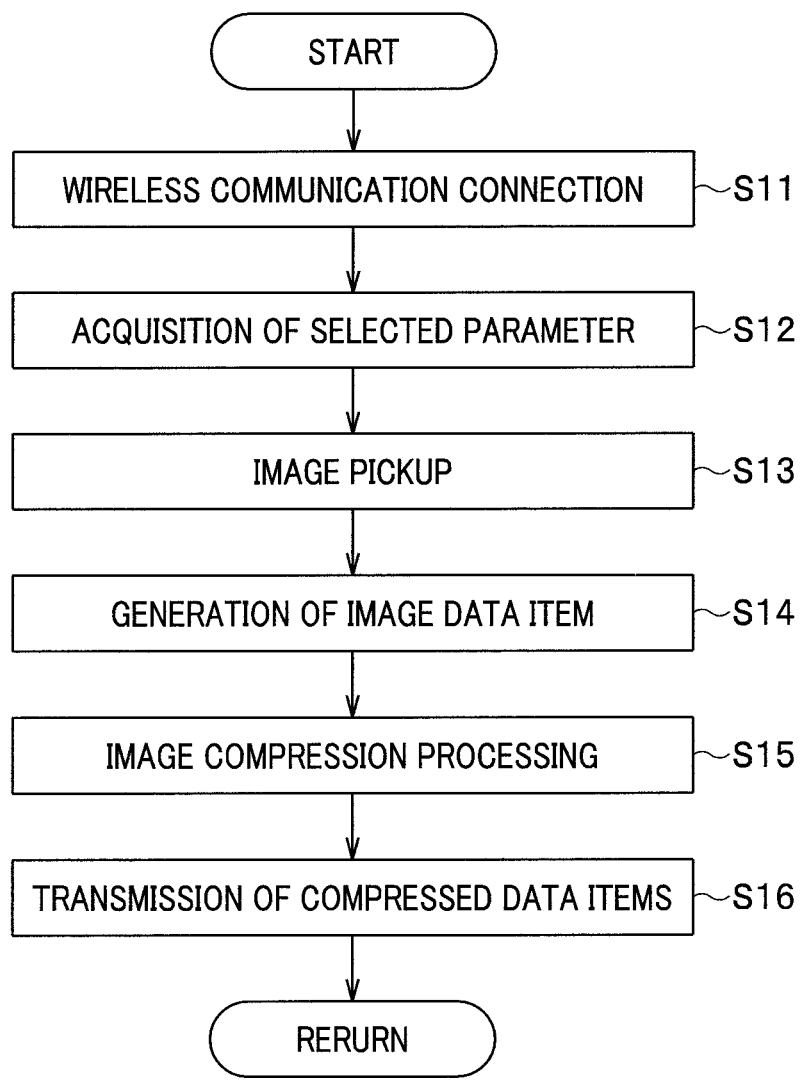
FIG. 4 is a flowchart illustrating an image data processing procedure in the endoscope illustrated in FIG. 2.

Next, an image data processing procedure in the endoscope 2 will be described with reference to FIGS. 2 and 4. FIG. 4 is a flowchart illustrating an image data processing procedure in the endoscope 2. Image data processing in the endoscope 2 includes compression processing in the compression processing control unit 51.

The image data processing in the endoscope 2 is performed by the endoscope control unit 22 and the compression processing control unit 51. Moreover, the image data processing in the endoscope 2 is started by an operation signal based on a user operation for providing an instruction to start image pickup processing being inputted to the endoscope control unit 22, and a processing sequence of steps S11 to S16 illustrated in FIG. 4 is repeatedly executed until an operation signal based on a user operation for providing an instruction to terminate the image pickup processing is inputted to the endoscope control unit 22. In the present embodiment, each time one image data item is generated, the processing sequence is executed once. Note that the operation signals are outputted, for example, from the non-illustrated user IF unit provided in the endoscope 2 or the user IF unit 36 provided in the processor 3.

In the image data processing in the endoscope 2, first, the endoscope control unit 22 establishes a wireless communication connection between the endoscope 2 and the processor 3 (step S11). Note that in image data processing performed for an N-th time (N is an integer of not less than 2), instead of the processing for establishing a wireless communication connection, whether or not a wireless communication connection is maintained may be confirmed, and if no wireless communication connection is maintained, the processing for establishing a wireless communication connection may be performed. If a wireless communication connection is maintained, the processing for establishing a wireless communication connection may be omitted.

Next, the compression processing control unit 51 acquires a selected parameter Q3 outputted from the compression parameter determining unit 53C (see FIG. 3) of the compression parameter arithmetic operation unit 53 (step S12). Note that as described later, the compression parameter determining unit 53C outputs the selected parameter Q3 to the second wireless communication unit 32A of the processor 3. The second wireless communication unit 32A transmits the outputted selected parameter Q3. The first wireless communication unit 23 of the endoscope 2 receives the transmitted selected parameter Q3. Moreover, in the present embodiment, the storage unit 52 is configured to be capable of storing the received selected parameter Q3. The compression processing control unit 51 acquires the selected parameter Q3 by reading the selected parameter Q3 from the storage unit 52. Moreover, in the processing sequence executed a first time, the compression processing control unit 51 acquires an initial value Qi of a compression parameter instead of the selected parameter Q3. For the initial value Qi, a set value inputted to the user IF unit 36 may be used or a set value stored in the storage units 37, 52 may be used.

Next, the endoscope control unit 22 controls the image pickup unit 21 to pick up an image of an object and generate an image data item, using power supplied from the battery 25 as a power source (steps S13 and S14). The image data item is outputted to the compression processing control unit 51. The image data item may be, for example, raw data.

Next, the compression processing control unit 51 performs compression processing for each of a plurality of unit areas of the image data item to perform image compression processing for generating a plurality of compressed data items from the image data item that is one image data item (step S15). Each of the plurality of compressed data items are sequentially stored in the storage unit 52. Note that the compression processing control unit 51 may sequentially read each of the plurality of unit areas of the image data item from the image pickup unit 21 and perform compression processing each time a unit area of the image data item is read.

Next, the endoscope control unit 22 controls the first wireless communication unit 23 to transmit the plurality of compressed data items stored in the storage unit 52 to the processor 3 (step S16). Next, if no operation signal based on a user operation for providing an instruction to terminate the image pickup processing is inputted to the endoscope control unit 22, the procedure returns to step S11, and if such operation signal is inputted to the endoscope control unit 22, the endoscope control unit 22 terminates the image data processing in the endoscope 2.

Note that an order of execution of the respective steps of the image data processing procedure in the endoscope 2 may be changed from the order illustrated in FIG. 4. For example, the processing for establishing a wireless communication connection (step S11) and the processing for acquiring the selected parameter Q3 (step S12) may be performed after the processing for picking up an image of an object and generating an image data item (steps S13 and S14). In this case, the image compression processing (step S15) is performed after the processing for acquiring the selected parameter Q3.

(Compression Processing and Transmission Processing)

Figure 8:
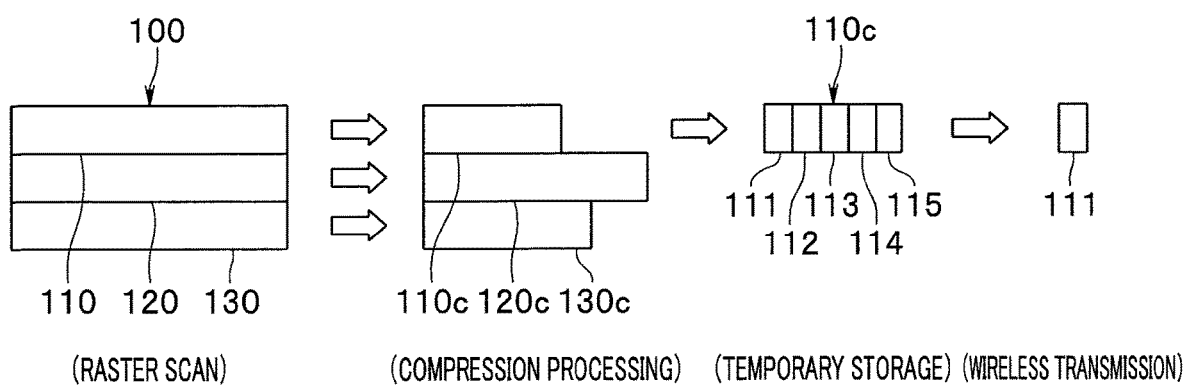
FIG. 8 is an explanatory diagram schematically illustrating an image data item and compressed data items in the first embodiment of the present invention.

The processing sequence in steps S15 and S16 will be described in detail below with reference to FIGS. 2 and 8. FIG. 8 is an explanatory diagram schematically illustrating an image data item and compressed data items. The compression processing control unit 51 performs compression processing for each of a plurality of unit areas of one image data item to generate a plurality of compressed data items from the one image data item. In FIG. 8, reference numeral 100 denotes one image data item. The image data item 100 corresponds to an image for one frame.

When the processing sequence of steps S11 to S16 illustrated in FIG. 4 is executed N times, compression processing is also performed N times. In the compression processing performed for an N-th time, first, the compression processing control unit 51 updates the compression parameter Q with the selected parameter Q3. In other words, the compression processing control unit 51 sets the acquired selected parameter Q3 as a new compression parameter Q. Note that in the compression processing performed a first time, the compression processing control unit 51 sets the initial value Qi as the compression parameter Q.

In the processing sequence in steps S15 and S16, next, the compression processing control unit 51 divides the image data item 100 into a plurality of areas. Here, for easy understanding, an example in which the image data item 100 is divided into three areas will be described. FIG. 8 illustrates an example in which a raster scan (scan in the right-left direction in FIG. 8) of the image data item 100 is performed to divide the image data item 100 into three areas 110, 120, 130. Each of the three areas 110, 120, 130 corresponds to a unit area.

Next, the compression processing control unit 51 performs compression processing for each unit area of the image data item 100 using the compression parameter Q to generate a plurality of compressed data items from the image data item 100. In the example illustrated in FIG. 8, the compression processing control unit 51 regards each of the three areas 110, 120, 130 as a unit area, and performs compression processing for each of the areas 110, 120, 130 to generate three compressed data items 110c, 120c, 130c. The compressed data item 110c is a data item generated by compression of the area 110, the compressed data item 120c is a data item generated by compression of the area 120 and the compressed data item 130c is a data item generated by compression of the area 130.

Note that when the compression processing control unit 51 sequentially reads each of the plurality of unit areas of the image data item from the image pickup unit 21 as described above, a processing sequence including processing for reading a unit area and compression processing for the read unit area is repeatedly performed a number of times, the number corresponding to the number of the unit areas.

The compression parameter Q is a value for defining a data amount after compression. For a compression format, an arbitrary image compression format can be used. The compression parameter Q has a correspondence relationship with a parameter for defining a compression rate in the compression format. In the present embodiment, it is defined that as the value of the compression parameter Q is larger, the compression rate becomes larger, that is, as the value of the compression parameter Q is larger, the data amount after compression becomes smaller.

Note that the data amount after compression varies depending not only on the value of the compression parameter Q but also on image information included in the unit area. In FIG. 8, respective lengths of the areas 110, 120, 130 and the compressed data items 110c, 120c, 130c schematically indicate respective data amounts. As illustrated in FIG. 8, even when the value of the compression parameter Q is the same and the respective data amounts of the areas 110, 120, 130 are the same, if respective image information pieces included in the areas. 110, 120, 130 are different from one another, respective data amounts of the compressed data items 110c, 120c, 130c are different from one another.

In the processing sequence in steps S15 and S16, next, each of the plurality of compressed data items is temporarily stored in the storage unit 52. More specifically, the compression processing control unit 51 sequentially outputs the plurality of compressed data items to the storage unit 52, and the storage unit 52 sequentially stores each of the plurality of compressed data items outputted. Next, the endoscope control unit 22 controls the first wireless communication unit 23 to sequentially read each of the plurality of compressed data items stored in the storage unit 52 and transmit each of the plurality of compressed data items.

More specifically, each of the compressed data items 110c, 120c, 130c is transmitted in the following manner. First, the compression processing control unit 51 outputs the compressed data item 110c to the storage unit 52. The storage unit 52 stores the compressed data item 110c. Next, the first wireless communication unit 23 reads the compressed data item 110c from the storage unit 52 and transmits the compressed data item 110c. Next, the compression processing control unit 51 outputs the compressed data item 120c to the storage unit 52. The storage unit 52 deletes the compressed data item 110c and stores the compressed data item 120c. Next, the first wireless communication unit 23 reads the compressed data item 120c from the storage unit 52 and transmits the compressed data item 120c. Next, the compression processing control unit 51 outputs the compressed data item 130c to the storage unit 52. The storage unit 52 deletes the compressed data item 120c and stores the compressed data item 130c. Next, the first wireless communication unit 23 reads the compressed data item 130c from the storage unit 52 and transmits the compressed data item 130c.

As described above, the storage unit 52 is used as a memory that temporarily stores a compressed data item. Note that the first wireless communication unit 23 performs reading processing and transmission processing for each of a plurality of unit packets of one compressed data item. In FIG. 8, each of reference numerals 111, 112, 113, 114, 115 denotes one of parts of the compressed data item 110c, the parts being obtained by division of the compressed data item 110c into respective unit packets. When the compressed data item 110c is transmitted, first, the first wireless communication unit 23 reads the part 111 from the storage unit 52 to generate a wireless signal and transmits the wireless signal. Subsequently, the first wireless communication unit 23 sequentially performs processing that is similar to the processing for the part 111, for the parts 112, 113, 114, 115.

(Image Data Processing in Processor)

Figure 5:
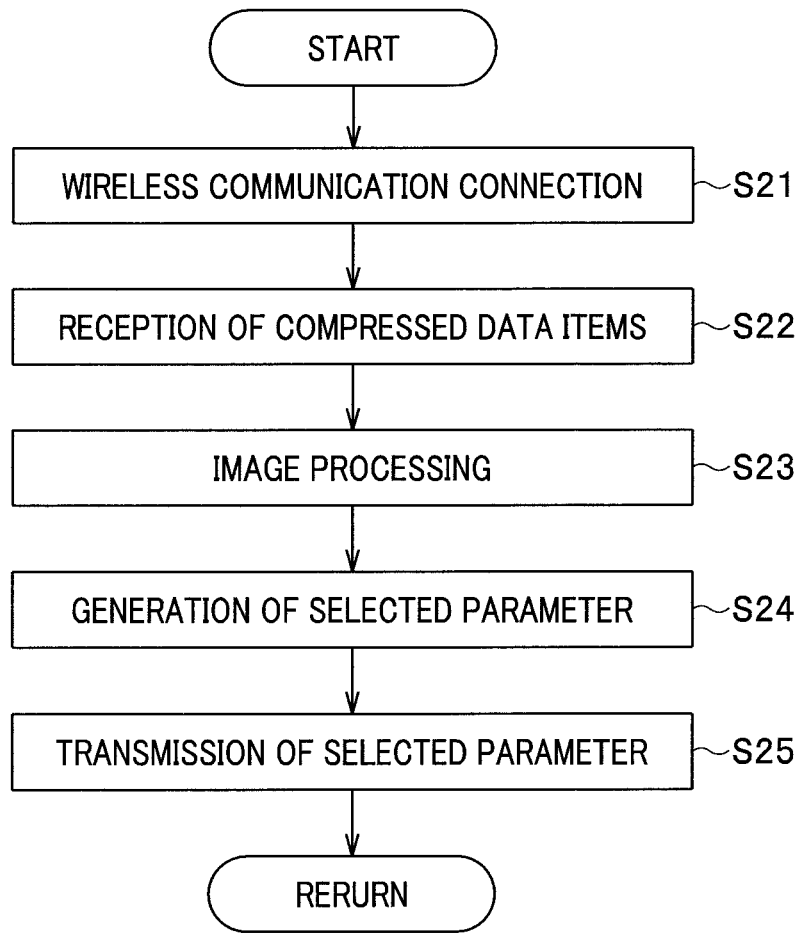
FIG. 5 is a flowchart illustrating an image data processing procedure in the processor illustrated in FIG. 2.

Next, an image data processing procedure in the processor 3 will be described with reference to FIGS. 2 and 5. FIG. 5 is a flowchart illustrating an image data processing procedure in the processor 3. Image data processing in the processor 3 includes processing for generating a first tentative compression parameter Q1 in the first compression parameter generating unit 53A, processing for generating a second tentative compression parameter Q2 in the second compression parameter generating unit 53B and processing for selecting a selected parameter Q3 in the compression parameter determining unit 53C.

The image data processing in the processor 3 is performed by the processor control unit 31 and the compression parameter arithmetic operation unit 53. Moreover, as with the image data processing in the endoscope 2, the image data processing in the processor 3 is started by an operation signal based on a user operation for providing an instruction for starting image pickup processing being inputted to the processor control unit 31, and a processing sequence of steps S21 to S25 illustrated in FIG. 5 is repeatedly executed until an operation signal based on a user operation for providing an instruction to terminate the image pickup processing is inputted to the processor control unit 31. In the present embodiment, each time one image data item is generated, the above processing sequence is executed once.

In the image data processing in the processor 3, first, the processor control unit 31 establishes a wireless communication connection between the endoscope 2 and the processor 3 (step S21). Note that in image data processing performed for an N-th time (N is an integer of not less than 2), instead of the processing for establishing a wireless communication connection, whether or not a wireless communication connection is maintained may be confirmed, and if no wireless communication connection is maintained, the processing for establishing a wireless communication connection may be performed. If a wireless communication connection is maintained, the processing for establishing a wireless communication connection may be omitted.

Next, the processor control unit 31 controls the second wireless communication unit 32A to receive the plurality of compressed data items transmitted by the first wireless communication unit 23 (step S22). The plurality of compressed data items received are stored in the storage unit 37.

Next, the processor control unit 31 controls the signal processing unit 33 to read the plurality of compressed data items from the storage unit 37 and performs predetermined image processing of the plurality of compressed data items (step S23). More specifically, as described above, the signal processing unit 33 performs decompression processing for each of the plurality of compressed data items and combines the decompressed data items to generate a non-compressed image data item (decompressed image data item).

Next, the compression parameter arithmetic operation unit 53 performs an arithmetic operation sequence relating to the compression parameter to generate a selected parameter Q3 (step S24). Next, the processor control unit 31 controls the second wireless communication unit 32A to transmit the selected parameter Q3 to the endoscope 2 (step S25). The first wireless communication unit 23 of the endoscope 2 receives the transmitted selected parameter Q3. Note that in the present embodiment, the storage unit 52 is configured to be capable of storing the selected parameter Q3. The first wireless communication unit 23 outputs the received selected parameter Q3 to the storage unit 52. The storage unit 52 stores the selected parameter Q3.

Next, if no operation signal based on a user operation for providing an instruction to terminate the image pickup processing is inputted to the processor control unit 31, the procedure returns to step S21, and if such operation signal is inputted to the processor control unit 31, the processor control unit 31 terminates the image data processing in the processor 3.

(Compression Parameter Arithmetic Operation Processing)

The arithmetic operation processing sequence relating to the compression parameter (hereinafter referred to as "compression parameter arithmetic operation processing") in step S24 will be described in detail below. In the compression parameter arithmetic operation processing, first tentative compression parameter generation processing in the first compression parameter generating unit 53A, second tentative compression parameter generation processing in the second compression parameter generating unit 53B and processing for selecting a selected parameter Q3 in the compression parameter determining unit 53C are performed. An order of performance of the first tentative compression parameter generation processing and the second tentative compression parameter generation processing can arbitrarily be determined. The processing for selecting a selected parameter Q3 is performed after performance of both the first tentative compression parameter generation processing and the second tentative compression parameter generation processing.

(First Tentative Compression Parameter Generation Processing)

Figure 6:
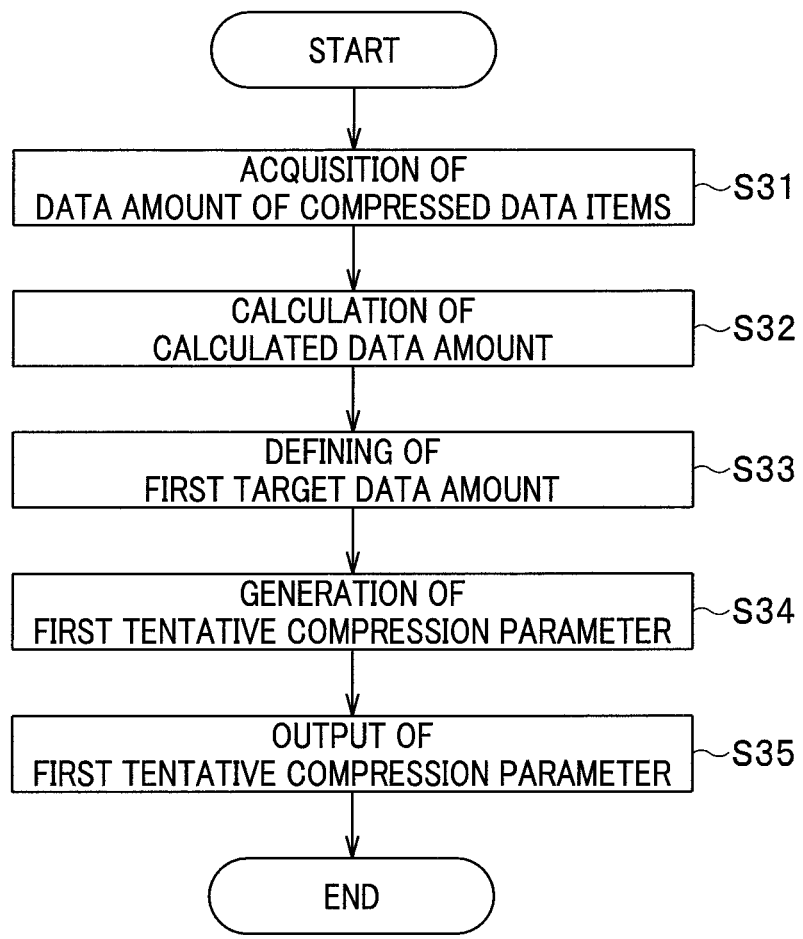
FIG. 6 is a flowchart illustrating a procedure of first tentative compression parameter generation processing procedure in the first embodiment of the present invention.

First, the first tentative compression parameter generation processing will be described with reference to FIGS. 2, 3 and 6. FIG. 6 is a flowchart illustrating a procedure of the first tentative compression parameter generation processing procedure. The first tentative compression parameter generation processing is performed by the first compression parameter generating unit 53A. In the first tentative compression parameter generation processing, first, the first compression parameter generating unit 53A acquires the respective data amounts of the plurality of compressed data items generated from the one image data item, which are stored in the storage unit 37 (step S31).

Next, the first compression parameter generating unit 53A performs an arithmetic operation including calculation of a total sum of the respective data amounts of the plurality of compressed data items generated from the one image data item, to calculate a calculated data amount (step S32). Since the calculated data amount has a correspondence relationship with the total sum of the respective data amounts of the plurality of compressed data items, the calculated data amount can be regarded as having a correspondence relationship with a data amount of the image data item compressed. Note that examples of the "arithmetic operation including calculation of a total sum of the respective data amounts of the plurality of compressed data items" include an arithmetic operation to obtain the total sum only and an arithmetic operation to divide the total sum by a predetermined coefficient after obtaining the total sum. Here, an example in which an arithmetic operation to obtain the total sum only is performed to calculate a calculated data amount V1 will be described. The calculated data amount V1 represents the data amount of the compressed image data item.

Next, the first compression parameter generating unit 53A acquires the transferable data amount from the transferable data amount calculating unit 35 and defines a first target data amount T1 based on the transferable data amount (step S33). The first target data amount T1 is defined so as to be smaller than the transferable data amount by, for example, subtracting a predetermined value from the transferable data amount or multiplying the transferable data amount by a predetermined coefficient of less than 1.

Moreover, the first target data amount T1 may be defined based on at least one of a pixel value distribution characteristic of respective color signals of the image data item (hereinafter simply referred to as "pixel value distribution characteristic"), an endoscope scene and a wireless environment in addition to the transferable data amount. The pixel value distribution characteristic is determined by an image pickup characteristic of the image pickup device and a spectral characteristic of the object. Information on the pixel value distribution characteristic can be acquired by, for example, an image data analyzing unit provided in the signal processing unit 33 analyzing the decompressed image data item. When the pixel values are distributed in a narrow range, image quality deterioration is small even if the compression rate is increased, and thus, the first target data amount T1 may be further decreased. On the other hand, when the pixel values are distributed in a wide range, image quality deterioration is large if the compression rate is increased, and thus, the first target data amount T1 may be further increased.

Examples of the endoscope scene include, e.g., a scene in which the insertion portion 2A is moved at a relatively high speed to reach a target region, a scene in which a search for determining whether or not there is an abnormal region is performed while the insertion portion 2A being moved and a scene in which a close observation or a predetermined treatment is performed. In a highly important scene, in order to prevent image quality deterioration, the first target data amount T1 may be further increased. On the other hand, in a less important scene, the first target data amount T1 is further decreased. Information on the endoscope scene can be obtained by, for example, the image data analyzing unit provided in the signal processing unit 33 analyzing the decompressed image data item or referring to a content manually set by the user using, e.g., the user IF unit 36.

When the first target data amount T1 is defined based on the wireless environment, for example, if the wireless communication environment deteriorates, the first target data amount T1 may be further decreased. Information on the wireless environment can be obtained, for example, from the transferable data amount calculating unit 35.

When the first target data amount T1 is defined based on the transferable data amount and a parameter other than the wireless environment, information of the above analysis result and/or information of the above set content are inputted to the first compression parameter generating unit 53A.

In the first tentative compression parameter generation processing, next, the first compression parameter generating unit 53A generates a first tentative compression parameter Q1 that is a compression parameter for performing compression processing for making the calculated data amount V1 be equal to or smaller than the first target data amount T1 (step S34). In the present embodiment, the first compression parameter generating unit 53A changes a magnitude of the first tentative compression parameter Q1 according to a difference between the calculated data amount V1 and the first target data amount T1. More specifically, the first compression parameter generating unit 53A calculates the first tentative compression parameter Q1 according to Equation (1) below.

$$Q1(n)=Q3(n-1)+A1*(V1-T1)/T1 \quad (1)$$

Note that in Equation (1), Q1(n) is a first tentative compression parameter Q1 calculated for a n-th time when the processing sequence of the image data processing in the processor 3 illustrated in FIG. 5 is executed n times n (n is an integer of not less than 1). Moreover, Q3(n-1) is a selected parameter Q3 selected for an n-1-th time. Q3(n-1) corresponds to a first tentative compression parameter Q1 calculated for the n-1-th time or a second tentative compression parameter Q2 calculated for the n-1-th time. The first compression parameter generating unit 53A reads Q3(n-1) from the storage unit 37 and calculates Q1(n). Moreover, A1 is a positive constant.

Note that a first tentative compression parameter Q1(1) calculated for a first time is calculated using a predetermined constant instead of Q3(n-1) in Equation (1). The predetermined constant may be the initial value Qi.

A reason that use of a first tentative compression parameter Q1 calculated using Equation (1) enables compression processing to be performed so as to make the calculated data amount V1 be equal to or smaller than the first target data amount T1 is as follows. The calculated data amount V1 corresponds to a calculated data amount when Q3(n-1) is used as the compression parameter. As can be understood from Equation (1), when the calculated data amount V1 is larger than the first target data amount T1, Q1(n) becomes larger than Q3(n-1), and as a result, a calculated data amount when Q1(n) is used as the compression parameter becomes small. Here, proper selection of a value of A1 enables making the calculated data amount when Q1(n) is used as the compression parameter be equal to or smaller than the first target data amount T1. In the present embodiment, the first tentative compression parameter Q1 that is a compression parameter for performing compression processing for making the calculated data amount V1 be equal to or smaller than the first target data amount T1 is generated in such a manner as above.

Note that as can be understood from Equation (1), when the calculated data amount V1 is smaller than the first target data amount T1, Q1(n) becomes smaller than Q3(n-1), and as a result, the calculated data amount when Q1(n) is used as the compression parameter becomes large. For the value of A1, a value that prevents the calculated data amount when Q1(n) is used as the compression parameter from becoming too large is selected. Moreover, as can be understood from Equation (1), when the calculated data amount V1 is equal to the first target data amount T1, Q1(n) is equal to Q3(n-1).

In the first tentative compression parameter generation processing, next, the first compression parameter generating unit 53A outputs the first tentative compression parameter Q1 to the compression parameter determining unit 53C (step S35). Consequently, the first tentative compression parameter generation processing ends.

The above description has been provided taking a case when a calculated data amount V1 is a total sum of respective data amounts of a plurality of compressed data items as an example. The calculated data amount may be a value obtained by dividing the total sum of the respective data amounts of the plurality of compressed data items by a number of the plurality of compressed data items, that is, an average value of the respective data amounts of the plurality of compressed data items. When the calculated data amount is the average value, a data amount corresponding to the average value is used as the first target data amount. More specifically, for example, the first target data amount may be obtained by subtracting a predetermined value from a value obtained by dividing the transferable data amount by the number of the plurality of compressed data items or may be obtained by multiplying a value obtained by dividing the transferable data amount by the number of the plurality of compressed data items, by a predetermined coefficient of less than 1.

Moreover, FIG. 6 indicates an example in which the first target data amount T1 is defined each time the first tentative compression parameter generation processing is performed. The parameters for determining the first target data amount T1 such as the wireless environment can vary each time the first tentative compression parameter generation processing is performed. Therefore, the first target data amount T1 can vary each time the first tentative compression parameter generation processing is performed.

Moreover, the method for calculating the first tentative compression parameter Q1 is not limited to the example indicated in Equation (1). For example, instead of A1 in Equation (1), the first tentative compression parameter Q1 may be calculated using a parameter that varies depending on at least one of the pixel value distribution characteristic, the endoscope scene and the wireless environment.

(Second Tentative Compression Parameter Generation Processing)

Figure 7:
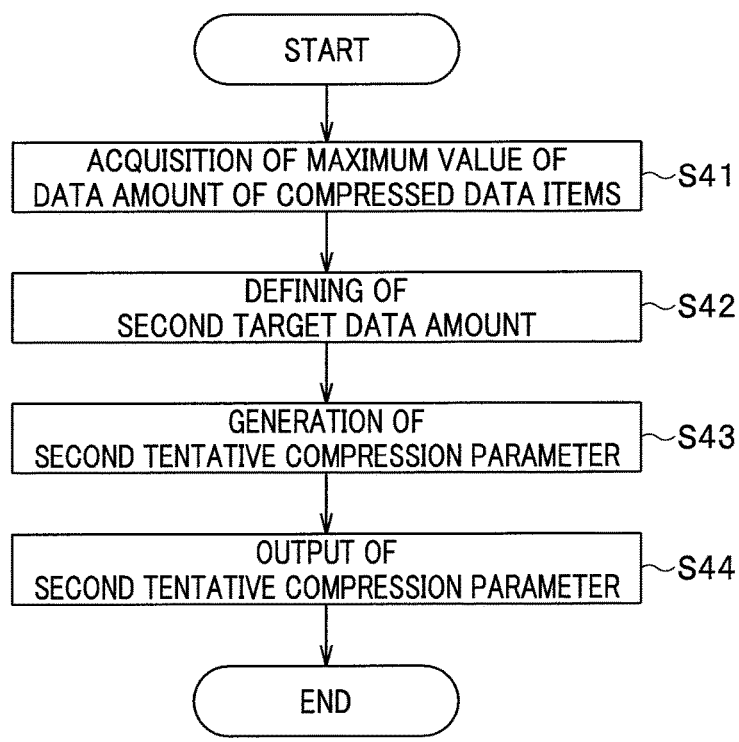
FIG. 7 is a flowchart illustrating a procedure of second tentative compression parameter generation processing in the first embodiment of the present invention.

Next, the second tentative compression parameter generation processing will be described with reference to FIGS. 2, 3 and 7. FIG. 7 is a flowchart illustrating a procedure of the second tentative compression parameter generation processing. The second tentative compression parameter generation processing is performed by the second compression parameter generating unit 53B. In the second tentative compression parameter generation processing, first, the second compression parameter generating unit 53B acquires a maximum value V2 of the respective data amounts of the plurality of compressed data items generated from the one image data item, which are stored in the storage unit 37 (step S41).

Next, the second compression parameter generating unit 53B acquires information of a storage capacity of the storage unit 52 and defines a second target data amount T2 based on the storage capacity of the storage unit 52 (step S42). The second target data amount T2 is defined so as to be smaller than the storage capacity of the storage unit 52 by, for example, subtracting a predetermined value from the storage capacity of the storage unit 52 or multiplying the storage capacity of the storage unit 52 by a predetermined coefficient of less than 1.

Next, the second compression parameter generating unit 53B generates a second tentative compression parameter Q2 that is a compression parameter for performing compression processing for making the maximum value V2 be equal to or smaller than the second target data amount T2 (step S43). In the present embodiment, the second compression parameter generating unit 53B changes a magnitude of the second tentative compression parameter Q2 according to a difference between the maximum value V2 and the second target data amount T2. More specifically, the second compression parameter generating unit 53B calculates the second tentative compression parameter Q2 according to Equation (2) below.

$$Q2(n)=Q3(n-1)+A2*(V2-T2)/T2 \quad (2)$$

Note that in Equation (2), Q2(n) is a second tentative compression parameter Q2 calculated for an n-th time (n is an integer of not less than 1) when the processing sequence of the image data processing in the processor 3 illustrated in FIG. 5 is performed. Moreover, as described above, Q3(n-1) is a selected parameter Q3 selected for an n-1-th time. The second compression parameter generating unit 53B reads Q3(n-1) from the storage unit 37 and calculates Q2(n). Moreover, A2 is a positive constant.

Note that a second tentative compression parameter Q2(1) calculated for a first time is calculated using a predetermined constant instead of Q3(n-1) in Equation (2). The predetermined constant may be the initial value Qi.

A reason that use of a second tentative compression parameter Q2 calculated using Equation (2) enables compression processing to be performed so as to make the maximum value V2 be equal to or smaller than the second target data amount T2 is as follows. The maximum value V2 corresponds to a maximum value of the respective data amounts of the plurality of compressed data items when Q3(n-1) is used as the compression parameter. As can be understood from Equation (2), when the maximum value V2 is larger than the second target data amount T2, Q2(n) becomes larger than Q3(n-1), and as a result, a maximum value of the respective data amounts of the plurality of compressed data items when Q2(n) is used as the compression parameter becomes small. Here, proper selection of a value of A2 enables making the maximum value of the respective data amounts of the plurality of compressed data items when Q2(n) is used as the compression parameter be equal to or smaller than the second target data amount T2. In the present embodiment, the second tentative compression parameter Q2 that is a compression parameter for performing compression processing for making the maximum value V2 be equal to or smaller than the second target data amount T2 is generated in such a manner as above.

Note that as can be understood from Equation (2), when the maximum value V2 is smaller than the second target data amount T2, Q2(n) becomes smaller than Q3(n-1), and as a result, the maximum value of the respective data amounts of the plurality of compressed data items when Q2(n) is used as the compression parameter becomes large. For the value of A2, a value that prevents the maximum value of the respective data amounts of the plurality of compressed data items when Q2(n) is used as a compression parameter from becoming too large is selected. Moreover, as can be understood from Equation (2), when the maximum value V2 is equal to the second target data amount T2, Q2(n) is equal to Q3(n-1).

In the second tentative compression parameter generation processing, next, the second compression parameter generating unit 53B outputs the second tentative compression parameter Q2 to the compression parameter determining unit 53C (step S44). Consequently, the second tentative compression parameter generation processing ends.

Note that FIG. 7 indicates an example in which the second target data amount T2 is defined each time the second tentative compression parameter generation processing is performed. In the present embodiment, the storage capacity of the storage unit 52 based on which the second target data amount T2 is defined is constant. Therefore, in the present embodiment, the processing for defining the second target data amount T2 (step S42) may be omitted. On the other hand, as in a third embodiment, which will be described later, when the storage capacity of the storage unit 52 varies, the second target data amount T2 can vary each time the second tentative compression parameter generation processing is performed.

(Selected Parameter Selection Processing)

Next, the selected parameter selection processing will be described with reference to FIG. 3. The selected parameter selection processing is performed by the compression parameter determining unit 53C. In the selected parameter selection processing, first, the compression parameter determining unit 53C compares the first tentative compression parameter Q1 generated by the first compression parameter generating unit 53A and the second tentative compression parameter Q2 generated by the second compression parameter generating unit 53B. Next, the compression parameter determining unit 53C selects a parameter that makes a data amount after compression be smaller from the first tentative compression parameter Q1 and the second tentative compression parameter Q2, as a selected parameter Q3. Next, the compression parameter determining unit 53C outputs the selected parameter Q3 to the storage unit 37 and the storage unit 52 provided in the endoscope 2. Consequently, the selected parameter selection processing ends.

As described above, in the present embodiment, the compression parameter Q is defined in such a manner that as a value of the compression parameter Q is larger, the data amount after compression becomes smaller. Therefore, as respective values of the first tentative compression parameter Q1 and the second tentative compression parameter Q2 are larger, the data amount after compression becomes smaller. Therefore, in the present embodiment, comparison in the compression parameter determining unit 53C is performed by comparison between the value of the first tentative compression parameter Q1 and the value of the second tentative compression parameter Q2. Moreover, in the present embodiment, a parameter having a larger value, of the first tentative compression parameter Q1 and the second tentative compression parameter Q2, is selected as the selected parameter Q3.

(Operation and Effects)

Next, operation and effects of the endoscope apparatus 1 according to the present embodiment will be described. In the present embodiment, as described above, the first tentative compression parameter Q1 and the second tentative compression parameter Q2 are compared to select a parameter that makes a data amount after compression be smaller as a selected parameter Q3. After the selection of the selected parameter Q3, the compression processing control unit 51 updates the compression parameter Q with the selected parameter Q3 and performs compression processing using the updated compression parameter Q. Consequently, according to the present embodiment, even when either one of the first tentative compression parameter Q1 and the second tentative compression parameter Q2 is selected as the selected parameter Q3, compression processing can be performed so as to make the calculated data amount be equal to or smaller than the first target data amount T1 and makes the maximum value of the respective data amounts of the plurality of compressed data items be equal to or smaller than the second target data amount T2. As a result, according to the present embodiment, compression processing can be performed so as to make the data amount of the compressed image data item be equal to or smaller than the transferable data amount and make each of the respective data amounts of the plurality of compressed data items be equal to or smaller than the storage capacity of the storage unit. Consequently, the present embodiment enables preventing interruption of image data transmission.

Moreover, in the present embodiment, the magnitude of the first tentative compression parameter Q1 is changed according to the difference between the calculated data amount V1 and the first target data amount T1, and the magnitude of the second tentative compression parameter Q2 is changed according to the difference between the maximum value V2 of the respective data amounts of the plurality of compressed data items and the second target data amount T2. More specifically, as indicated in Equation (1), Q1(n) is calculated in such a manner that: as an absolute value of a difference V1−T1 is larger, a difference between Q1(n) and Q3(n-1) becomes larger; and if the difference V1−T1 has a positive value, Q1(n) becomes larger than Q3(n-1) and if the difference V1−T1 has a negative value, Q1(n) becomes smaller than Q3(n-1). Likewise, as indicated in Equation (2), Q2(n) is calculated in such a manner that: as an absolute value of a difference V2−T2 is larger, a difference between Q2(n) and Q3(n-1) becomes larger; and if the difference V2−T2 has a positive value, Q2(n) becomes larger than Q3(n-1) and if the difference V2−T2 has a negative value, Q2(n) becomes smaller than Q3(n-1).

Figure 9:
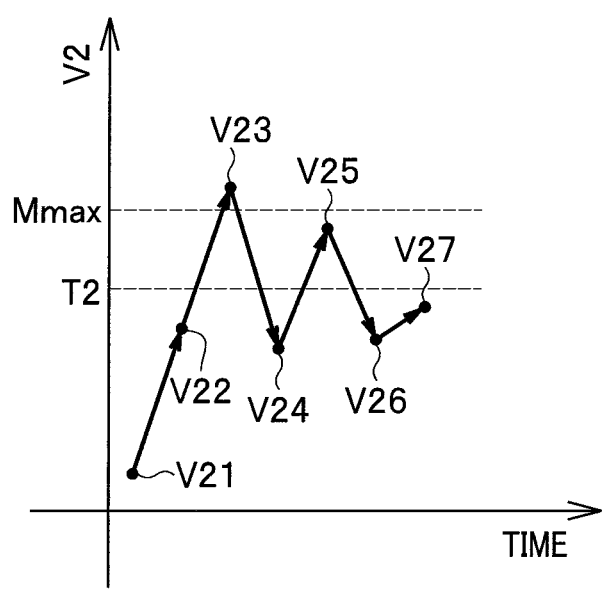
FIG. 9 is an explanatory diagram schematically illustrating changes in a maximum value of data amounts of compressed data items in the first embodiment of the present invention.

According to the present embodiment, as described above, calculation of the first and second tentative compression parameters Q1, Q2 enables bringing the calculated data amount V1 close to the first target data amount T1 and bringing the maximum value V2 close to the second target data amount T2. FIG. 9 is an explanatory diagram schematically illustrating changes in the maximum value V2. In FIG. 9, the horizontal axis represents time and the vertical axis represents a magnitude of the maximum value V2. The maximum value V2 is calculated a plurality of times at predetermined intervals. In FIG. 9, maximum values V21, V22, V23, V24, V25, V26, V27 calculated in the order mentioned are connected with arrows. The maximum value V21 is a maximum value V2 when compression processing was performed using the initial value Qi as the compression parameter Q. Each of the maximum values V22 to V27 is a maximum value V2 when compression processing was performed using a selected parameter Q3 generated by performing the compression parameter arithmetic operation processing in the present embodiment, as the compression parameter Q.

As illustrated in FIG. 9, when the maximum value V2 is smaller than the second target data amount T2, the maximum value V2 for a next time becomes larger and when the maximum value V2 is larger than the second target data amount T2, the maximum value V2 for a next time becomes smaller. Proper selection of A2 in Equation (2) gradually brings the maximum value V2 close to the second target data amount T2.

Note that FIG. 9 indicates an example in which the initial value Qi was set to be relatively large. Therefore, as illustrated in FIG. 9, the maximum value V21 becomes smaller than the maximum values V22 to V27. Moreover, the maximum value V23 indicates an example in which a magnitude of the maximum value V23 is larger than a size Mmax of the storage capacity of the storage unit 52. In this case, it is impossible to store the compressed data items, and thus, transmission of the image data item is interrupted. If transmission of the image data item is interrupted, for example, the video output unit 34 (see FIG. 2) displays an image data item successfully transmitted last time on the monitor 4 (see FIG. 1).

The content described with reference to FIG. 9 applies also to the calculated data amount V1 and the first target data amount T1. In other words, proper selection of A1 in Equation (1) gradually brings the calculated data amount V1 close to the first target data amount T1.

Moreover, in the present embodiment, the compression parameter arithmetic operation unit 53 is provided in the processor 3. Consequently, the present embodiment enables reducing power consumed by the endoscope 2 in comparison with a case where the compression parameter arithmetic operation unit 53 is provided in the endoscope 2.

Moreover, in the present embodiment, when the first target data amount T1 is defined based on the transferable data amount only and A1 in Equation (1) is set to be a constant, the first tentative compression parameter Q1 can be calculated without analyzing the image data item. Consequently, according to the present embodiment, the processing for calculating the first tentative compression parameter Q1 is simplified and there is no need for an image data analyzing unit, and as a result, an arithmetic operation amount relating to the compression parameter can be reduced. On the other hand, when the first target data amount T1 is defined based on at least one of the pixel value distribution characteristic, the endoscope scene and the wireless environment in addition to the transferable data amount, and the first tentative compression parameter Q1 is calculated using a parameter that varies depending on at least one of the pixel value distribution characteristic, the endoscope scene and the wireless environment instead of A1, the compression parameter can flexibly be changed according to a change in situation.

Note that in the present embodiment, in N-th image data processing (see FIG. 4) in the endoscope 2, basically, a selected parameter Q3(n-1) selected in n-1-th image data processing (see FIG. 5) in the processor 3 is used. In other words, in N-th image data processing in the endoscope 2, the compression processing control unit 51 acquires the selected parameter Q3(n-1) from the storage unit 52 and uses the acquired selected parameter Q3(n-1) as a new compression parameter Q. However, for example, there is a case when information from the processor 3 temporarily fails to be received because of, e.g., a wireless communication failure and Q3(n-1) cannot be received at the time of performance of N-th image data processing in the endoscope 2. In this case, the compression processing control unit 51 cannot acquire the selected parameter Q3(n-1) from the storage unit 52.

On the other hand, in the present embodiment, the storage unit 52 is configured to be capable of storing a selected parameter Q3. In the present embodiment, when the compression processing control unit 51 cannot acquire a selected parameter Q3(n-1) in N-th image data processing in the endoscope 2, the compression processing control unit 51 acquires a selected parameter Q3(m) selected before the selected parameter Q3(n-1), the selected parameter Q3(m) being stored in the storage unit 52. Note that m is an integer that is not less than 1 but not more than n-2 and is closest to n-1. Consequently, according to the present embodiment, it is possible to, even when Q3(n-1) cannot be acquired in the N-th image data processing in the endoscope 2, update the compression parameter Q with the selected parameter Q3(m).

Moreover, in the present embodiment, compression processing of all unit areas included in one image data item is performed using the same compression parameter Q. However, the endoscope apparatus 1 according to the present embodiment may be configured to perform compression processing for a plurality of image data items, using the same compression parameter Q. In this case, each time compression processing (step S15 in FIG. 4), and image processing (step S23 in FIG. 5) in the signal processing unit 33 for one image data item are performed a plurality of times, processing for acquiring a selected parameter Q3 (step S12 in FIG. 4), compression parameter arithmetic operation processing (step S24 in FIG. 5) and processing for transmitting the selected parameter Q3 (step S25 in FIG. 5) are performed once.

Second Embodiment

Figure 10:
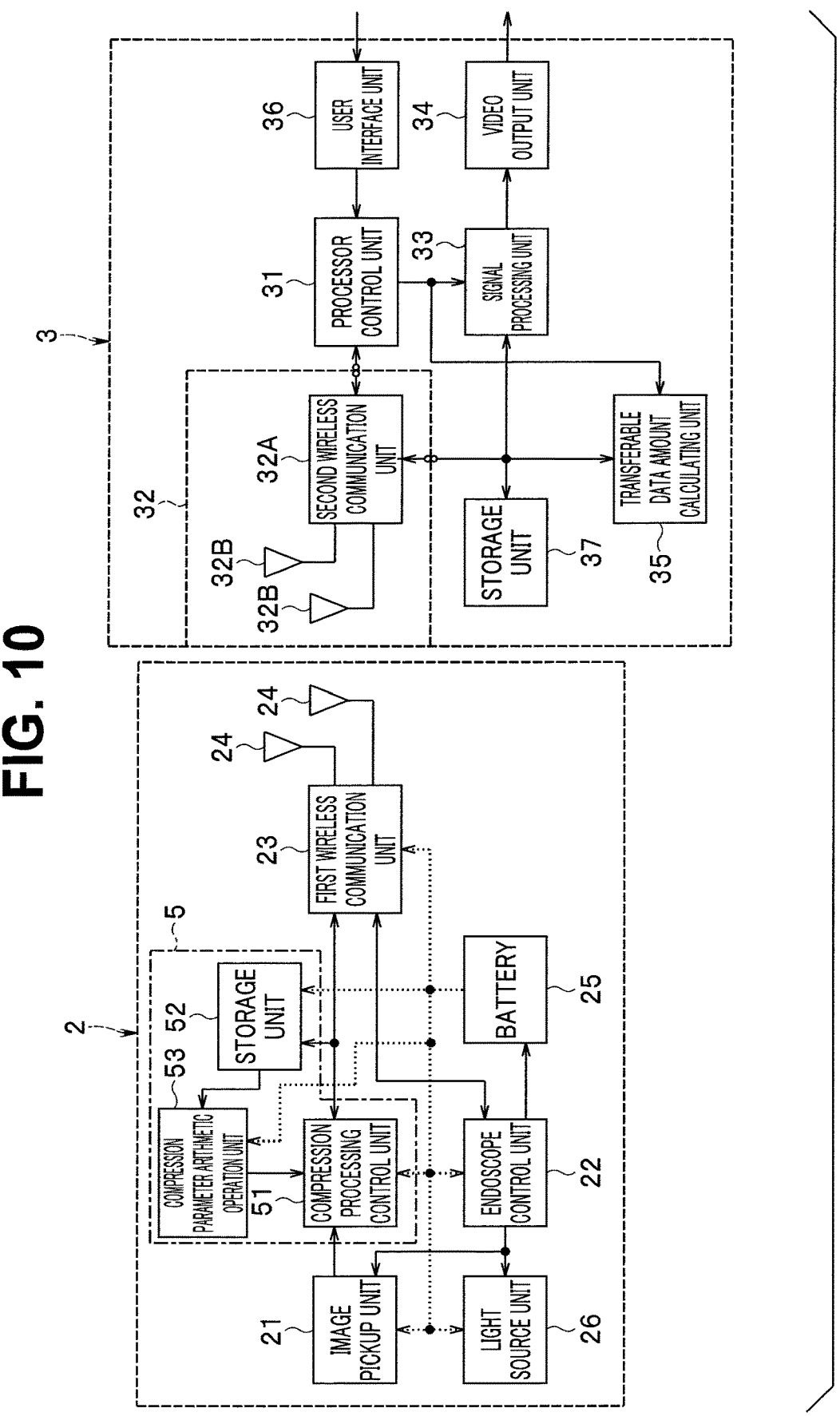
FIG. 10 is a functional block diagram illustrating configurations of an endoscope, a processor and an image compression device in an endoscope apparatus according to a second embodiment of the present invention.

Next, a wireless endoscope apparatus according to a second embodiment of the present invention will be described with reference to FIG. 10. FIG. 10 is a functional block diagram illustrating configurations of an endoscope 2, a processor 3 and an image compression device 5. In the present embodiment, an entirety of the image compression device 5 is provided in the endoscope 2. In other words, in the present embodiment, in addition to a compression processing control unit 51 and a storage unit 52 of the image compression device 5, a compression parameter arithmetic operation unit 53 of the image compression device 5 is also provided in the endoscope 2.

A configuration of the compression parameter arithmetic operation unit 53 in the present embodiment is the same as the configuration illustrated in FIG. 3 in the first embodiment. As illustrated in FIG. 3, the compression parameter arithmetic operation unit 53 includes a first compression parameter generating unit 53A, a second compression parameter generating unit 53B and a compression parameter determining unit 53C.

In the present embodiment, the first compression parameter generating unit 53A is configured to be capable of acquiring respective data amounts of a plurality of compressed data items stored in the storage unit 52 and a transferable data amount calculated by a transferable data amount calculating unit 35 of the processor 3. Moreover, the second compression parameter generating unit 53B is configured to be capable of acquiring a maximum value of the respective data amounts of the plurality of compressed data items stored in the storage unit 52. Moreover, the compression parameter determining unit 53C is configured to output a selected parameter Q3 directly to the compression processing control unit 51.

A battery 25 in the present embodiment is configured to be capable of supplying power to the compression parameter arithmetic operation unit 53 as a power supply unit.

Figure 11:
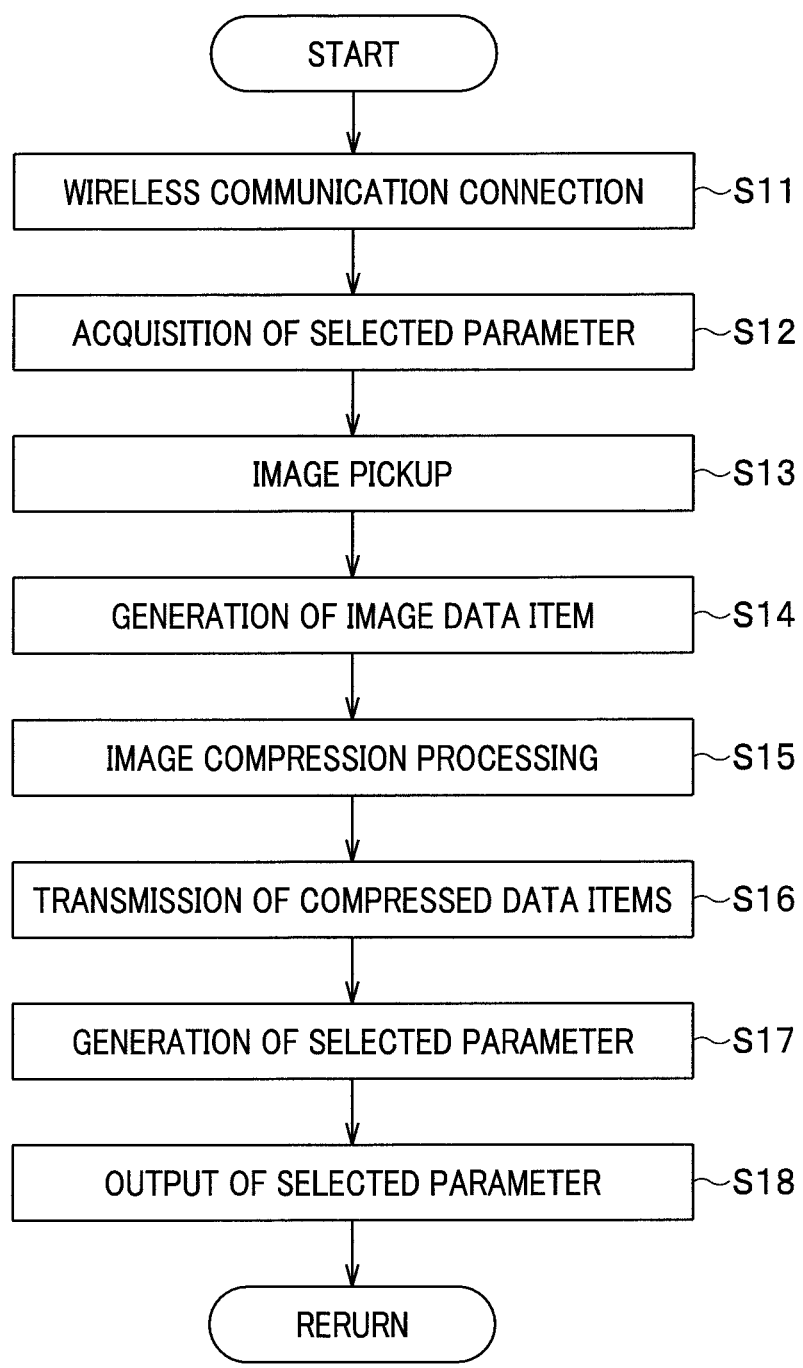
FIG. 11 is a flowchart illustrating an image data processing procedure in the endoscope illustrated in FIG. 10.

Next, image data processing procedure in the endoscope 2 of the present embodiment will be described with reference to FIGS. 10 and 11. FIG. 11 is a flowchart illustrating an image data processing procedure in the endoscope 2. The image data processing procedure in endoscope 2 of the present embodiment includes compression processing in the compression processing control unit 51, processing for generating a first tentative compression parameter Q1 in the first compression parameter generating unit 53A, processing for generating a second tentative compression parameter Q2 in the second compression parameter generating unit 53B and processing for selecting a selected parameter Q3 in the compression parameter determining unit 53C.

Image data processing in the endoscope 2 of the present embodiment is performed by an endoscope control unit 22, the compression processing control unit 51 and the compression parameter arithmetic operation unit 53. The image data processing procedure in the endoscope 2 of the present embodiment is the same as the procedure illustrated in FIG. 4 in the first embodiment until processing for transmitting a plurality of compressed data items (step S16). In the present embodiment, next, compression parameter arithmetic operation processing in which a selected parameter is generated by performing an arithmetic operation sequence relating to a compression parameter is performed (step S17). The content of step S17 is similar to the content of step S24 illustrated in FIG. 5 in the first embodiment. Next, the compression parameter arithmetic operation unit 53 performs processing for outputting the selected parameter to the compression processing control unit 51 (step S18). Next, if no operation signal based on a user operation for providing an instruction to terminate the image pickup processing is inputted to the endoscope control unit 22, the procedure returns to step S11, and if such operation signal is inputted to the endoscope control unit 22, the image data processing in the endoscope 2 is terminated.

Figure 12:
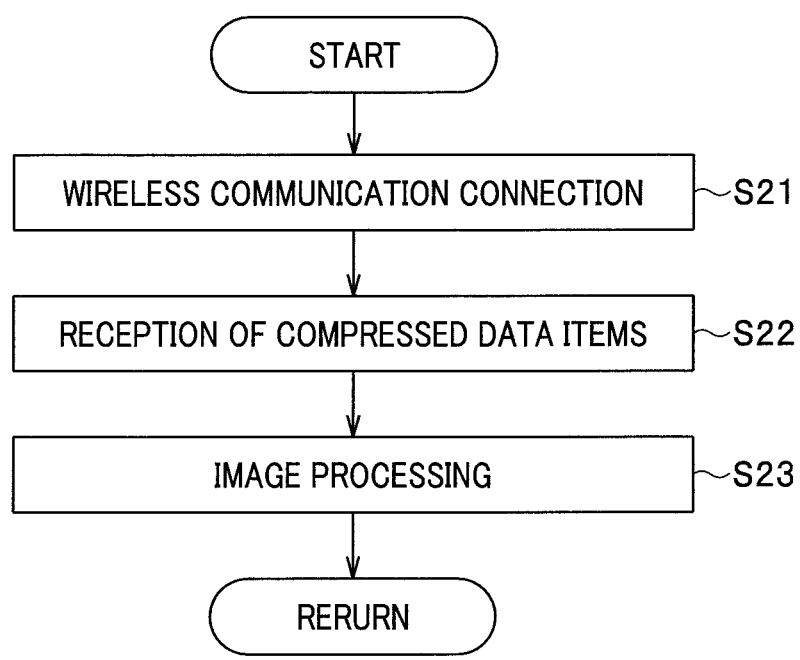
FIG. 12 is a flowchart illustrating an image data processing procedure in the processor illustrated in FIG. 10.

Next, an image data processing procedure in the processor 3 of the present embodiment will be described with reference to FIGS. 10 and 12. FIG. 12 is a flowchart illustrating an image data processing procedure in the processor 3. Image data processing in the processor 3 of the present embodiment is performed by a processor control unit 31. The image data processing procedure in the processor 3 of the present embodiment is basically the same as the procedure illustrated in FIG. 5 in the first embodiment. However, in the present embodiment, steps S24 and S25 illustrated in FIG. 5 are not executed. In other words, after performance of predetermined image processing for a plurality of compressed data items (step S23), if no operation signal based on a user operation for providing an instruction to terminate the image pickup processing is inputted to the processor control unit 31, the procedure returns to step S21, and if such operation signal is inputted to the processor control unit 31, the image data processing in the processor 3 is terminated.

Next, operation and effects of the endoscope apparatus 1 according to the present embodiment will be described. In the present embodiment, the compression parameter determining unit 53C is configured to output the selected parameter Q3 directly to the compression processing control unit 51. Consequently, according to the present embodiment, for example, even when information from the processor 3 temporarily fails to be received because of, e.g., a wireless communication failure, a compression parameter Q can be updated with the selected parameter Q3. Note that as in the first embodiment, in the present embodiment, also, the storage unit 52 may be configured to be capable of storing the selected parameter Q3. In this case, the compression parameter determining unit 53C outputs the selected parameter Q3 also to the storage unit 52.

Moreover, in the example illustrated in FIGS. 11 and 12, compression processing of all unit areas included in one image data item is performed using the same compression parameter Q. However, the endoscope apparatus 1 according to the present embodiment may be configured to perform compression processing using different compression parameters Q for each set of one or more unit areas included in one image data item. In this case, compression processing for a set of one or more unit areas (step S15 in FIG. 11), processing for transmitting the compressed data item(s) (step S16 in FIG. 11), compression parameter arithmetic operation processing (step S17 in FIG. 11) and processing for transmitting a selected parameter (step S18 in FIG. 11) may be performed a plurality of times to complete the compression processing for the one image data item.

In the present embodiment, the effect provided by the compression parameter arithmetic operation unit 53 being provided in the processor 3, which has been described in the first embodiment, cannot be obtained. The rest of the configuration, operation and effects of the present embodiment is similar to that of the first embodiment.

Third Embodiment

Figure 13:
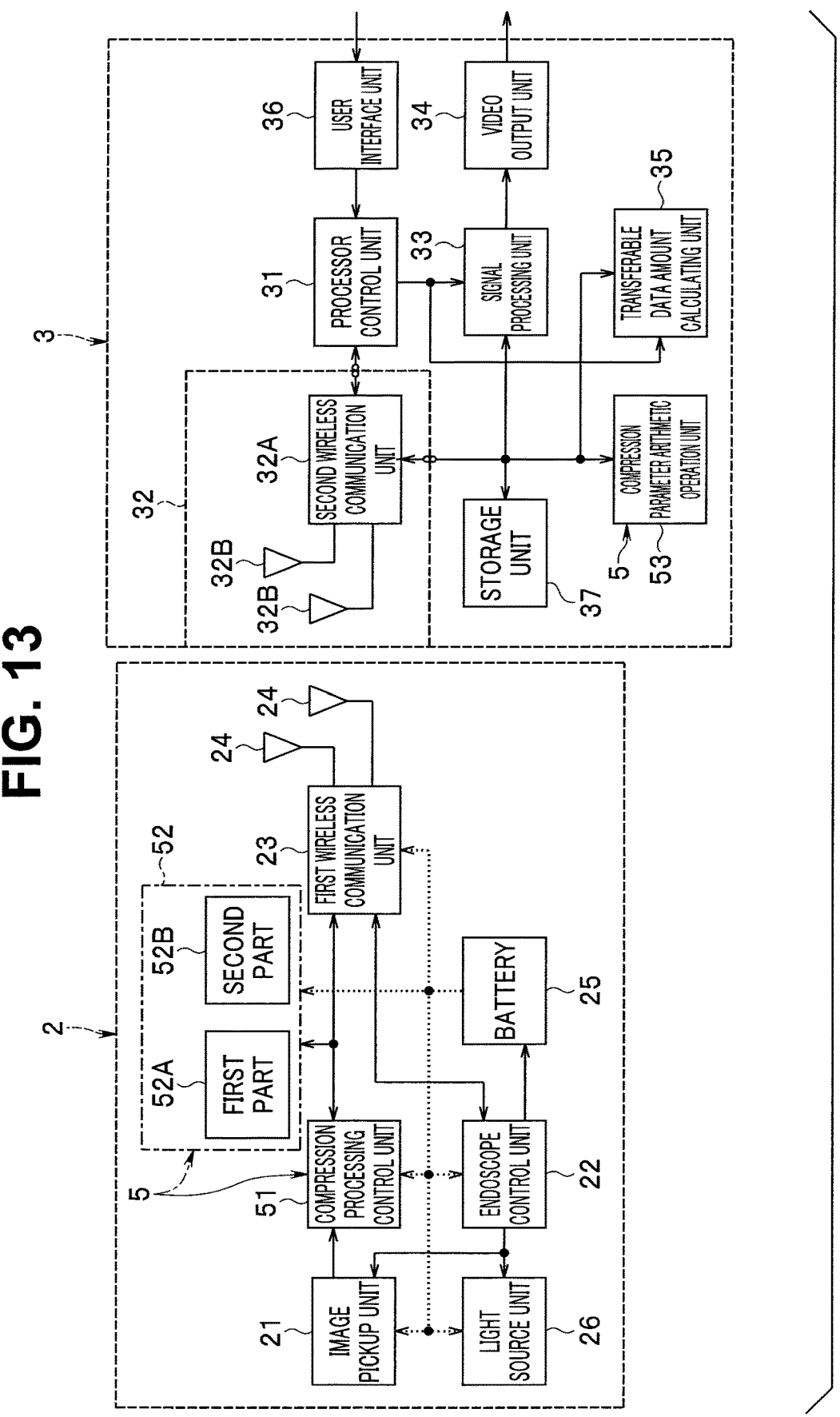
FIG. 13 is a functional block diagram illustrating configurations of an endoscope, a processor and an image compression device in an endoscope apparatus according to a third embodiment of the present invention.

Next, a wireless endoscope apparatus according to a third embodiment the present invention will be described with reference to FIG. 13. FIG. 13 is a functional block diagram illustrating configurations of an endoscope 2, a processor 3 and an image compression device 5. In the present embodiment, a storage unit 52 of the image compression device 5 includes a plurality of parts each having a constant storage capacity. FIG. 13 indicates an example in which the storage unit 52 includes a first part 52A and a second part 52B as the plurality of parts. Each of the first and second parts 52A, 52B is configured by a rewritable storage element such as a RAM. The storage capacity of the first part 52A and the storage capacity of the second part 52B may be the same or may be different from each other.

A storage capacity of the storage unit 52 is a sum of the storage capacity of the first part 52A and the storage capacity of the second part 52B. In the present embodiment, it is possible to control activation and stoppage of each of the first part 52A and the second part 52B. If both the first part 52A and the second part 52B are activated, the storage capacity of the storage unit 52 is the sum of the storage capacity of the first part 52A and the storage capacity of the second part 52B. Moreover, if one of the first part 52A and the second part 52B is stopped and the other is activated, the storage capacity of the storage unit 52 is equal to the storage capacity of the activated part. In this way, in the present embodiment, the storage capacity of the storage unit 52 is changeable.

As the storage capacity of the storage unit 52 is larger, a data amount of a compressed data item that can be stored in the storage unit 52 becomes larger, which, however, results in an increase in power consumed and amount of heat generated in the endoscope 2. Therefore, when a data amount of a compressed data item is small, it is preferable to stop a part of the storage unit 52 to reduce power consumed and an amount of heat generated in the endoscope 2. In the present embodiment, the storage capacity of the storage unit 52 can be changed by controlling activation and stoppage of each of the first part 52A and the second part 52B according to a data amount of a compressed data item.

Control of activation and stoppage of each of the first part 52A and the second part 52B may be performed based on a data amount of an compressed data item. Alternatively, the above control may be performed based on first and second tentative compression parameters Q1, Q2. In other words, when a maximum value V2 of respective data amounts of a plurality of compressed data items becomes larger than a second target data amount T2 defined based on the storage capacity of the storage unit 52, there is a possibility that a compressed data item fails to be stored in the storage unit 52. This possibility becomes higher as a difference between the maximum value V2 and the second target data amount T2 is larger, that is, the second tentative compression parameter Q2 is larger. Therefore, for example, if the second tentative compression parameter Q2 is larger than the first tentative compression parameter Q1 or a difference between the first tentative compression parameter Q1 and the second tentative compression parameter Q2 becomes equal to or below a predetermined threshold value, it is assumed that there is a high possibility of a failure of a compressed data item to be stored in the storage unit 52 and both the first part 52A and the second part 52B are activated to increase the storage capacity of the storage unit 52. In a case other than the above case, one of the first part 52A and the second part 52B is stopped. Consequently, according to the present embodiment, it is possible to reduce power consumed and an amount of heat generated in the endoscope 2 while preventing a failure of a compressed data item to be stored in the storage unit 52.

Note that in the present embodiment, as in the second embodiment, an entirety of the image compression device 5 may be provided in the endoscope 2. The rest of the configuration, operation and effects of the present embodiment is similar to that of the first or second embodiment.

The present invention is not limited to the above-described embodiments, and various changes, alterations and the like are possible without departing from the gist of the present invention. For example, an endoscope apparatus of the present invention may be an endoscope apparatus having a configuration in which an endoscope and a processor are connected via a universal cable. In the endoscope apparatus having such configuration, a transmission path through an image data item is transmitted is configured by a wired transmission path in its entirety and includes no wireless transmission path.

Moreover, an image compression device of the present invention may be configured to be used for transmitting an image data item to an external apparatus other than the relevant endoscope apparatus. In this case, a transmission path through which an image data item is transmitted may include a wireless transmission path or may include no wireless transmission path.

Moreover, a compression parameter arithmetic operation unit 53 may be provided in each of both an endoscope 2 and a processor 3. In this case, for example, the compression parameter arithmetic operation unit 53 provided in the endoscope 2 may define a first target data amount T1 based on a transferable data amount only and calculate a first tentative compression parameter Q1 with A1 in Equation (1) set as a constant, and the compression parameter arithmetic operation unit 53 provided in the processor 3 may define a first target data amount T1 based on at least one of a pixel value distribution characteristic, an endoscope scene and a wireless environment in addition to the transferable data amount and calculate a first tentative compression parameter Q1 using a parameter that varies depending on at least one of the pixel value distribution characteristic, the endoscope scene and the wireless environment instead of A1. A second tentative compression parameter Q2 may be calculated in one of the compression parameter arithmetic operation unit 53 provided in the endoscope 2 and the compression parameter arithmetic operation unit 53 provided in the processor 3.

What is claimed is:

1. An endoscope apparatus comprising:
an image pickup device configured to pick up an image of an object and generate an image data item; and
an image compression device configured to compress the image data item, wherein
the image compression device includes a storage element having a storage capacity of a predetermined size, and
the image compression device is configured to
perform compression processing for each of a plurality of unit areas of the image data item using a compression parameter to generate a plurality of compressed data items from the image data item that is one image data item,
store each of the plurality of compressed data items in the storage element,
generate a first compression parameter for performing compression processing in such a manner that a calculated data amount calculated by performing an arithmetic operation including calculation of a total sum of respective data amounts of the plurality of compressed data items becomes equal to or smaller than a first target data amount defined based on a transferable data amount that is an amount of data transferable in a transmission path for the image data item, generate a second compression parameter for performing compression processing in such a manner that a maximum value of the respective data amounts of the plurality of compressed data items becomes equal to or smaller than a second target data amount defined based on the storage capacity, compare the first compression parameter and the second compression parameter to select a parameter with which a data amount after compression is smaller as a selected parameter, and update the compression parameter with the selected parameter.

2. The endoscope apparatus according to claim 1, wherein the calculated data amount is the total sum of the respective data amounts of the plurality of compressed data items.

3. The endoscope apparatus according to claim 1, wherein the calculated data amount is a value obtained by dividing the total sum of the respective data amounts of the plurality of compressed data items by a number of the plurality of compressed data items.

4. The endoscope apparatus according to claim 1, wherein the image compression device changes a magnitude of the first compression parameter according to a difference between the calculated data amount and the first target data amount.

5. The endoscope apparatus according to claim 1, wherein the image compression device changes a magnitude of the second compression parameter according to a difference between the maximum value of the respective data amounts of the plurality of compressed data items and the second target data amount.

6. The endoscope apparatus according to claim 1, wherein the image compression device selects the selected parameter by comparing respective values of the first compression parameter and the second compression parameter.

7. The endoscope apparatus according to claim 1, wherein:

the storage element is further configured to be capable of storing the selected parameter; and the image compression device acquires the selected parameter stored in the storage element and updates the compression parameter with the acquired selected parameter.

8. The endoscope apparatus according to claim 1, wherein the first target data amount is defined based on the transferable data amount and at least one of a distribution characteristic of pixel values of respective color signals of the image data, an endoscope scene and a wireless environment.

9. The endoscope apparatus according to claim 1, further comprising a processor, wherein the processor is configured to successively calculate the transferable data amount.

10. The endoscope apparatus according to claim 1, wherein the storage capacity is constant.

11. The endoscope apparatus according to claim 1, wherein the storage capacity is changeable.

12. The endoscope apparatus according to claim 11, wherein the storage capacity is changed by controlling activation and stoppage of a part of the storage element.

13. The endoscope apparatus according to claim 1, further comprising:

a first wireless communication circuit configured to transmit the plurality of compressed data items stored in the storage element;

a second wireless communication circuit configured to receive the plurality of compressed data items transmitted;

a monitor; and a processor, wherein the processor is configured to perform predetermined image processing for the plurality of compressed data items received, and the monitor displays a result of the image processing.

14. The endoscope apparatus according to claim 13, wherein:

the processor is further configured to successively calculate the transferable data amount; and the processor calculates the transferable data amount based on a wireless communication environment.

15. The endoscope apparatus according to claim 13, further comprising:

an endoscope in which the image pickup device is mounted; and a video processor physically separated from the endoscope, wherein the second wireless communication circuit and the processor are provided in the video processor, the image compression device performs the generation of the first compression parameter, the generation of the second compression parameter and the selection of the selected parameter in the video processor, the storage element and the first wireless communication circuit are provided in the endoscope, the image compression device generates the plurality of compressed data items in the endoscope, the second wireless communication circuit transmits the selected parameter, and the first wireless communication circuit receives the selected parameter transmitted.

16. The endoscope apparatus according to claim 13, further comprising:

an endoscope in which the image pickup device is mounted; and a video processor physically separated from the endoscope, wherein the second wireless communication circuit and the processor are provided in the video processor, and the image compression device and the first wireless communication circuit are provided in the endoscope.

17. A compression method for compressing an image data item generated by an image pickup device of an endoscope, the compression method comprising:

performing compression processing for each of a plurality of unit areas of the image data item using a compression parameter to generate a plurality of compressed data items from the image data item that is one image data item, and storing each of the plurality of compressed data items in a storage element having a storage capacity of a predetermined size;

generating a first compression parameter for performing compression processing in such a manner that a calculated data amount calculated by performing an arithmetic operation including calculation of a total sum of respective data amounts of the plurality of compressed data items stored becomes equal to or smaller than a first target data amount defined based on a transferable data amount that is an amount of data transferable in a transmission path for the image data item;

generating a second compression parameter for performing compression processing in such a manner that a maximum value of the respective data amounts of the plurality of compressed data items becomes equal to or smaller than a second target data amount defined based on the storage capacity;

comparing the first compression parameter and the second compression parameter to select a parameter with which a data amount after compression is smaller as a selected parameter; and compressing a newly acquired image data item using the compression parameter.

18. A non-transitory computer-readable recording medium recording a program for a computer to execute, the program being provided to compress an image data item generated by an image pickup device of the endoscope, the program causing the computer to:

perform compression processing for each of a plurality of unit areas of the image data item using a compression parameter to generate a plurality of compressed data items from the image data item that is one image data item, and store each of the plurality of compressed data items in a storage element having a storage capacity of a predetermined size;

generate a first compression parameter for performing compression processing in such a manner that a calculated data amount calculated by performing an arithmetic operation including calculation of a total sum of respective data amounts of the plurality of compressed data items stored becomes equal to or smaller than a first target data amount defined based on a transferable data amount that is an amount of data transferable in a transmission path for the image data item;

generate a second compression parameter for performing compression processing in such a manner that a maximum value of the respective data amounts of the plurality of compressed data items becomes equal to or smaller than a second target data amount defined based on the storage capacity;

compare the first compression parameter and the second compression parameter to select a parameter with which a data amount after compression is smaller as a selected parameter; and compress a newly acquired image data item using the compression parameter.

\* \* \* \* \*